US008258305B2

(12) United States Patent
Hauske

(10) Patent No.: US 8,258,305 B2
(45) Date of Patent: Sep. 4, 2012

(54) DOPAMINE TRANSPORTER INHIBITORS FOR USE IN TREATMENT OF MOVEMENT DISORDERS AND OTHER CNS INDICATIONS

(75) Inventor: James R. Hauske, La Jolla, CA (US)

(73) Assignee: Prexa Pharmaceuticals, Inc., Boston, MA (US)

( * ) Notice: Subject to any disclaimer, the term of this patent is extended or adjusted under 35 U.S.C. 154(b) by 1004 days.

(21) Appl. No.: 11/884,965

(22) PCT Filed: Feb. 21, 2006

(86) PCT No.: PCT/US2006/006338
§ 371 (c)(1),
(2), (4) Date: Sep. 5, 2008

(87) PCT Pub. No.: WO2006/091697
PCT Pub. Date: Aug. 31, 2006

(65) Prior Publication Data
US 2010/0217727 A1   Aug. 26, 2010

Related U.S. Application Data

(60) Provisional application No. 60/655,978, filed on Feb. 23, 2005.

(51) Int. Cl.
| A61P 25/00 | (2006.01) |
| A61K 31/445 | (2006.01) |
| C07D 211/00 | (2006.01) |
| C07D 401/00 | (2006.01) |

(52) U.S. Cl. ........ 546/197; 546/201; 546/207; 546/216; 546/225; 546/229; 546/240; 546/336
(58) Field of Classification Search ............ 546/197, 546/201, 207, 216, 225, 229, 240, 336
See application file for complete search history.

(56) References Cited

U.S. PATENT DOCUMENTS

| 7,294,637 B2 * | 11/2007 | Aquila et al. ............ 514/317 |
| 7,517,892 B2 * | 4/2009 | Aquila et al. ............ 514/317 |
| 7,816,375 B2 * | 10/2010 | Aquila et al. ............ 514/317 |
| 2009/0054489 A1 * | 2/2009 | Hauske ............ 514/326 |
| 2010/0093706 A1 | 4/2010 | Hauske |

FOREIGN PATENT DOCUMENTS

| JP | 2003-500392 A | 1/2003 |
| JP | 2004-509103 A | 3/2004 |
| WO | WO-91/09032 A1 | 6/1991 |
| WO | WO-0071518 A2 | 11/2000 |
| WO | WO-01/44193 A1 | 6/2001 |
| WO | WO-02/22572 A2 | 3/2002 |
| WO | WO-2006/091697 A1 | 8/2006 |
| WO | WO-2006/091702 A2 | 8/2006 |
| WO | WO-2008024371 A2 | 2/2008 |

OTHER PUBLICATIONS

Morissette et al., Advanced Drug Delivery REv., vol. 56, 2004, pp. 275-300.*
Patani et al., Chem Rev., 1996, vol. 96, pp. 3147-3176.*
International Search Report for PCT/US2007/018522 dated Mar. 19, 2008.
International Search Report for PCT/US2006/006338 dated Aug. 8, 2006.
International Search Report for PCT/US2006/006347 dated Aug. 7, 2006.
U.S. Appl. No. 11/884,961, James R. Hauske.

* cited by examiner

*Primary Examiner* — Susannah Chung
(74) *Attorney, Agent, or Firm* — Mintz Levin Cohn Ferris Glovsky and Popeo, P.C.; Heidi A. Erlacher; Lian Ouyang

(57) ABSTRACT

The invention provides a class of dopamine transporter inhibitors of formula (I) (DAT inhibitors), packaged pharmaceuticals comprising such inhibitors, and their uses in treating, or manufacturing medicaments for treating disease conditions including Parkinson's disease, when assessed by one or more of Hoehn and Yahr Staging of Parkinson's Disease, Unified Parkinson Disease Rating Scale (UPDRS), and Schwab and England Activities of Daily Living Scale. Related business methods such as marketing the inhibitors to healthcare providers are also provided.

16 Claims, 4 Drawing Sheets

DOPAMINE TRANSPORTER INHIBITORS FOR USE IN TREATMENT OF MOVEMENT DISORDERS AND OTHER CNS INDICATIONS

RELATED APPLICATIONS

This application is a national stage filing under 35 U.S.C. 371 of International Application PCT/US2006/006338, filed Feb. 21, 2006, which claims the benefit of priority to U.S. Provisional Patent Application No. 60/655,978, filed on Feb. 23, 2005. International Application PCT/US2006/006338 was published under PCT Article 21(2) in English.

BACKGROUND OF THE INVENTION

A movement disorder is a neurological disturbance that involves one or more muscles or muscle groups. Movement disorders affect a significant portion of the population, causing disability as well as distress. Movement disorders include Parkinson's disease, Huntington's chorea, progressive supranuclear palsy, Wilson's disease, Tourette's syndrome, epilepsy, tardive dyskinesia, and various chronic tremors, tics and dystonias. Different clinically observed movement disorders can be traced to the same or similar areas of the brain. For example, abnormalities of basal ganglia (a large cluster of cells deep in the hemispheres of the brain) are postulated as a causative factor in diverse movement disorders.

Parkinson's disease is a movement disorder of increasing occurrence in aging populations. Parkinson's disease is a common disabling disease of old age affecting about one percent of the population over the age of 60 in the United States. The incidence of Parkinson's disease increases with age and the cumulative lifetime risk of an individual developing the disease is about 1 in 40. Symptoms include pronounced tremor of the extremities, bradykinesia, rigidity and postural change. A perceived pathophysiological cause of Parkinson's disease is progressive destruction of dopamine producing cells in the basal ganglia which comprise the pars compartum of the substantia nigra, basal nuclei located in the brain stem. Loss of dopamineric neurons results in a relative excess of acetylcholine. Jellinger, K. A., Post Mortem Studies in Parkinson's Disease—Is It Possible to Detect Brain Areas For Specific Symptoms?, J Neural Transm 56 (Supp); 1-29: 1999. Parkinson's disease is a progressive disorder which can begin with mild limb stiffness and infrequent tremors and progress over a period of ten or more years to frequent tremors and memory impairment, to uncontrollable tremors and dementia.

Tardive dyskinesia (TD) is a chronic disorder of the nervous system, characterized by involuntary, irregular rhythmic movements of the mouth, tongue, and facial muscles. The upper extremities also may be involved. These movements may be accompanied, to a variable extent, by other involuntary movements and movement disorders. These include rocking, writhing, or twisting movements of the trunk (tardive dystonia), forcible eye closure (tardive blepharospasm), an irresistible impulse to move continually (tardive akathisia), jerking movements of the neck (tardive spasmodic torticollis), and disrupted respiratory movements (respiratory dyskinesia). The vast majority of TD cases are caused by the prolonged use of antipsychotic drugs (neuroleptics). A relatively small number are caused by the use of other medications, such as metoclopramide, that, like neuroleptics, block dopamine receptors. TD often manifests or worsens in severity after neuroleptic drug therapy is discontinued. Resumption of neuroleptic therapy will temporarily suppress the involuntary movements, but may aggravate them in the long run.

Tardive dyskinesia affects approximately 15-20% of patients treated with neuroleptic drugs (Khot et al., Neuroleptics and Classic Tardive Dyskinesia, in Lang A E, Weiner W J (eds.): Drug Induced Movement Disorders, Futura Publishing Co., 1992, pp 121-166). Therefore, the condition affects hundreds of thousands of people in the United States alone. The cumulative incidence of TD is substantially higher in women, in older people, and in those being treated with neuroleptics for conditions other than schizophrenia, such as bipolar disorder (manic-depressive illness) (see, e.g., Hayashi et al., Clin. Neuropharmacol, 19:390, 1996; Jeste et al., Arch. Gen. Psychiatry, 52:756, 1995). Unlike the acute motor side effects of neuroleptic drugs, TD does not respond in general to antiparkinson drugs (Decker et al., New Eng. J Med., Oct. 7, p. 861, 1971).

Focal dystonias are a class of related movement disorders involving the intermittent sustained contraction of a group of muscles. The prevalence of focal dystonias in one US county was estimated as 287 per million (Monroe County Study); this suggests that at least 70,000 people are affected in the US alone. The spasms of focal dystonia can last many seconds at a time, causing major disruption of the function of the affected area. Some of the focal dystonias are precipitated by repetitive movements; writer's cramp is the best known example. Focal dystonia can involve the face (e.g., blepharospasm, mandibular dystonia), the neck (torticollis), the limbs (e.g., writer's cramp), or the trunk. Dystonia can occur spontaneously or can be precipitated by exposure to neuroleptic drugs and other dopamine receptor blockers (tardive dystonia). No systemic drug therapy is generally effective, but some drugs give partial relief to some patients. Those most often prescribed are anticholinergics, baclofen, benzodiazepines, and dopamine agonists and antagonists. The most consistently effective treatment is the injection of botulinum toxin into affected muscles.

The various focal dystonias tend to respond to the same drugs (Chen, Clin. Orthop, June, 102-6, 1998; Esper et al; Term. Med, January, 90:18-20, 1997; De Mattos et al., Arq. Neuropsychiatry, March 54:30-6, 1996) This suggests that a new treatment helpful for one focal dystonia would be likely to be helpful for another. Furthermore, the common symptoms, signs, and responses to medication of spontaneous (idiopathic) dystonia and neuroleptic-induced dystonia suggest that an effective treatment for a drug-induced focal dystonia will be effective for the same dystonia occurring spontaneously.

A tic is an abrupt repetitive movement, gesture, or utterance that often mimics a normal type of behavior. Motor tics include movements such as eye blinking, head jerks or shoulder shrugs, but can vary to more complex purposive appearing behaviors such as facial expressions of emotion or meaningful gestures of the arms and head. In extreme cases, the movement can be obscene (copropraxia) or self injurious. Phonic or vocal tics range from throat clearing sounds to complex vocalizations and speech, sometimes with coprolalia (obscene speech) (Leckman et al., supra). Tics are irregular in time, though consistent regarding the muscle groups involved. Characteristically, they can be suppressed for a short time by voluntary effort.

Tics are estimated to affect 1% to 13% of boys and 1% to 11% of girls, the male-female ratio being less than 2 to 1. Approximately 5% of children between the ages of 7 and 11 years are affected with tic behavior (Leckman et al., Neuropsychiatry of the Bas. Gang, December, 20(4): 839-861, 1997). The estimated prevalence of multiple tics with vocalization, i.e. Tourette's syndrome, varies among different reports, ranging from 5 per 10,000 to 5 per 1,000. Tourette's syndrome is 3-4 times more common in boys than girls and 10 times more common in children and adolescents than in adults (Leckman et al., supra; Esper et al, Term. Med. 90:18-20, 1997).

Gilles de la Tourette syndrome (TS) is the most severe tic disorder. Patients with TS have multiple tics, including at least one vocal (phonic) tic. TS becomes apparent in early childhood with the presentation of simple motor tics, for example, eye blinking or head jerks. Initially, tics may come and go, but in time tics become persistent and severe, and begin to have adverse effects on the child and the child's family. Phonic tics manifest, on average, 1 to 2 years after the onset of motor tics. By the age of 10, most children have developed an awareness of the premonitory urges that frequently precede a tic. Such premonitions may enable the individual to voluntary suppress the tic, yet premonition unfortunately adds to the discomfort associated with having the disorder. By late adolescence/early adulthood, tic disorders can improve significantly in certain individuals. However, adults who continue to suffer from tics often have particularly severe and debilitating symptoms. (Leckman et al., supra).

Although the present day pharmacopeia offers a variety of agents to treat movement disorders, none of these agents can prevent or cure these conditions. Furthermore, the most effective treatments are often associated with intolerable side effects. There remains a clear-cut need for new treatments for movement disorders that have greater efficacy and fewer side effects than those currently available.

SUMMARY OF THE INVENTION

The present invention relates to the discovery of certain dopamine transporter inhibitors (collectively referred to herein as the subject "DAT inhibitors"), and the use of those inhibitors in methods of treatment, and the production of packaged pharmaceuticals and pharmaceutical preparations. The subject DAT inhibitors are represented by Formula I, or are a pharmaceutically acceptable salt, solvate, metabolite or pro-drug thereof:

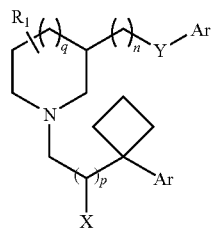

(I)

wherein, as valence and stability permit,
Ar, independently for each occurrence, represents a substituted or unsubstituted aryl or heteroaryl ring;
X represents —H or —OR;
Y represents —O—, —S—, —C(R)$_2$—, or ≧N(R)—;
R, independently for each occurrence, represents —H or lower alkyl;
R$_1$ represents one or more substituents to the ring to which it is attached, such as halogen, amino, acylamino, amidino, cyano, nitro, azido, ether, thioether, sulfoxido, -J-R$_2$, -J-OH, -J-lower alkyl, -J-lower alkenyl, -J-R$_2$, -J-SH, -J-NH$_2$, or substituted or unsubstituted lower alkyl, lower alkenyl, cycloalkyl, heterocyclyl, cycloalkylalkyl, heterocyclylalkyl, aryl, heteroaryl, aralkyl, or heteroaralkyl, or protected forms of the above;
R$_2$, independently for each occurrence, represents H or substituted or unsubstituted lower alkyl, cycloalkyl, heterocyclyl, aralkyl, heteroaralkyl, aryl, or heteroaryl;
J represents, independently for each occurrence, a chain having from 0-8 (preferably from 0-4) units selected from —C(R)$_2$—, —N(R)—, —O—, and —S—;
n is an integer from 0 to 2;
p is 0 or 1; and
q is an integer from 0 to 2, preferably 1.

In another embodiment, the invention provides a packaged pharmaceutical comprising: a DAT inhibitor of any of the invention in an amount sufficient to treat or prevent a movement disorder and formulated in a pharmaceutically acceptable carrier; and instructions (written and/or pictorial) describing the use of the formulation for treating the patient. The movement disorder may be selected from ataxia, corticobasal ganglionic degeneration (CBGD), dyskinesia, dystonia, tremors, hereditary spastic paraplegia, Huntington's disease, multiple system atrophy, myoclonus, Parkinson's disease, progressive supranuclear palsy, restless legs syndrome, Rett syndrome, spasticity, Sydenham's chorea, other choreas, athetosis, ballism, stereotypy, tardive dyskinesia/dystonia, tics, Tourette's syndrome, olivopontocerebellar atrophy (OPCA), diffuse Lewy body disease, hemibalismus, hemi-facial spasm, restless leg syndrome, Wilson's disease, stiff man syndrome, akinetic mutism, psychomotor retardation, painful legs moving toes syndrome, a gait disorder, a drug-induced movement disorder, or other movement disorder. The DAT inhibitor may be provided in an amount sufficient to treat or prevent a movement disorder in a patient by a statistically significant amount when assessed by one or more of Hoehn and Yahr Staging of Parkinson's Disease, Unified Parkinson Disease Rating Scale (UPDRS), and Schwab and England Activities of Daily Living Scale. The DAT inhibitor may be provided in an amount sufficient to treat or prevent a movement disorder in a patient by a statistically significant amount when assessed by a standardized test in combination with an empirical test selected from computer tomography (CT), magnetic resonance imaging (MRI), and positron emission tomography (PET).

In some embodiments, the packaged pharmaceutical may further comprise another medication selected from dopamine precursors, dopaminergic agents, dopaminergic and anti-cholinergic agents, anti-cholinergic agents, dopamine agonists, MAO-B (monoamine oxidase B) inhibitors, COMT (catechol O-methyltransferase) inhibitors, muscle relaxants, sedatives, anticonvulsant agents, dopamine reuptake inhibitors, dopamine blockers, β-blockers, carbonic anhydrase inhibitors, narcotic agents, GABAergic agents, or alpha antagonists.

In another embodiment, the packaged pharmaceutical is provided in an escalating dose which produces an escalating serum concentration of said DAT inhibitor(s) over a period of at least 4 hours.

In another embodiment, the invention provides for the use of a DAT inhibitor of the invention in the manufacture of a pharmaceutical composition for prophylaxis or treatment of a patient susceptible to or suffering from a movement disorder. The movement disorder may be selected from ataxia, corticobasal ganglionic degeneration (CBGD), dyskinesia, dystonia, tremors, hereditary spastic paraplegia, Huntington's disease, multiple system atrophy, myoclonus, Parkinson's disease, progressive supranuclear palsy, restless legs syndrome, Rett syndrome, spasticity, Sydenham's chorea, other choreas, athetosis, ballism, stereotypy, tardive dyskinesia/dystonia, tics, Tourette's syndrome, olivopontocerebellar atrophy (OPCA), diffuse Lewy body disease, hemibalismus, hemi-facial spasm, restless leg syndrome, Wilson's disease, stiff man syndrome, akinetic mutism, psychomotor retardation, painful legs moving toes syndrome, a gait disorder, a drug-induced movement disorder, or other movement disorder. The use may be for treatment of a human patient.

In some embodiments of the invention, the packaged pharmaceutical or use may be for oral administration. In some embodiments of the packaged pharmaceutical or use, the DAT inhibitor may be formulated as a transdermal patch.

In another embodiment, the invention provides a method for treating a movement disorder comprising administering to the patient a composition of a DAT inhibitor of the invention in an amount sufficient to treat the movement disorder in the animal as evaluated by a standardized test. The movement disorder may be selected from ataxia, corticobasal ganglionic degeneration (CBGD), dyskinesia, dystonia, tremors, hereditary spastic paraplegia, Huntington's disease, multiple system atrophy, myoclonus, Parkinson's disease, progressive supranuclear palsy, restless legs syndrome, Rett syndrome, spasticity, Sydenham's chorea, other choreas, athetosis, ballism, stereotypy, tardive dyskinesia/dystonia, tics, Tourette's syndrome, olivopontocerebellar atrophy (OPCA), diffuse Lewy body disease, hemibalismus, hemi-facial spasm, restless leg syndrome, Wilson's disease, stiff man syndrome, akinetic mutism, psychomotor retardation, painful legs moving toes syndrome, a gait disorder, a drug-induced movement disorder, or other movement disorder. The DAT inhibitor may be provided in an amount sufficient to treat a movement disorder in a patient by a statistically significant amount when assessed by one or more of Hoehn and Yahr Staging of Parkinson's Disease, Unified Parkinson Disease Rating Scale (UPDRS), and Schwab and England Activities of Daily Living Scale. The DAT inhibitor may be provided in an amount sufficient to treat or prevent a movement disorder in a patient by a statistically significant amount when assessed by a standardized test in combination with an empirical test selected from computer tomography (CT), magnetic resonance imaging (MRI), and positron emission tomography (PET).

In some embodiments, the method may comprise coadministation of the DAT inhibitor with one or more of a dopamine precursor, a dopaminergic agent; a dopaminergic and anti-cholinergic agent, an anti-cholinergic agent, a dopamine agonist, a MAO-B (monoamine oxidase B) inhibitor, a COMT (catechol O-methyltransferase) inhibitor, a muscle relaxant, a sedative, an anticonvulsant agent, a dopamine reuptake inhibitor, a dopamine blocker, a β-blocker, a carbonic anhydrase inhibitor, a narcotic agent, a GABAergic agent, or an alpha antagonist.

In another embodiment, the invention provides a method for conducting a pharmaceutical business, comprising: (a) manufacturing the packaged pharmaceutical of the invention; and (b) marketing to healthcare providers the benefits of using the package or preparation to treat patients suffering from a movement disorder.

In another embodiment, the invention provides a method for conducting a pharmaceutical business, comprising: (a) providing a distribution network for selling the packaged pharmaceutical of the invention; and (b) providing instruction material to patients or physicians for using the package or preparation to treat patients suffering from a movement disorder.

In another embodiment, the invention provides a method for conducting a pharmaceutical business, comprising: (a) determining an appropriate dosage of an DAT inhibitor of the invention to enhance function performance in a class of patients suffering from a movement disorder; (b) conducting therapeutic profiling of one or more formulations of the DAT inhibitor identified in step (a), for efficacy and toxicity in animals; and (c) providing a distribution network for selling a the formulations identified in step (b) as having an acceptable therapeutic profile. The method may include an additional step of providing a sales group for marketing the preparation to healthcare providers.

In another embodiment, the invention provides a method for conducting a medical assistance reimbursement program, comprising: (a) providing a reimbursement program which permits, for prescription of a DAT inhibitors of the invention for treating a movement order, at least partial reimbursement to a healthcare provider or patient, or payment to a drug distributor; (b) processing one or more claims for prescription of an DAT inhibitors for treating a movement order; and (c) reimbursing the healthcare provider or patient, or paying a drug distributor, at least a portion of the cost of said prescription.

In another embodiment, the invention provides a method for treating depression, a sleep disorder, obesity, attention deficit disorder (ADD), attention deficit hyperactivity disorder (ADHD), sexual dysfunction, or substance abuse comprising administering to the patient a composition of a DAT inhibitor of the invention in an amount sufficient to treat the movement disorder in the animal as evaluated by a standardized test.

The practice of the present invention will employ, unless otherwise indicated, conventional techniques of synthetic chemistry, organic chemistry, inorganic chemistry, organometallic chemistry, pharmaceutical chemistry, and behavioral science, which are within the skill of the art. Such techniques are described in the literature. See, for example, Advanced Organic Chemistry: Reactions, Mechanisms, And Structure by J. March (John Wiley and Sons, N.Y., 1992); The Chemist's Companion: A Handbook Of Practical Data, Techniques, And References by A. J. Gordon and R. A. Ford (Wiley, NY, 1972); Synthetic Methods Of Organometallic And Inorganic Chemistry by W. A. Herrmann and Brauer (Georg Thieme Verlag, N.Y., 1996); Experimental Organic Chemistry by D. Todd (Prentice-Hall, N.J., 1979); Experimental Organic Chemistry: Standard And Microscale by L. M. Harwood (Blackwell Science, M.A., 1999); Experimental Analysis Of Behavior by I. H. Iversen and K. A. Lattal (Elsevier, N.Y., 1991); A Practical Guide To Behavioral Research: Tools And Techniques by R. Sommer and B. Sommer (Oxford University Press, N.Y., 2002); Advances In Drug Discovery Techniques by A. L. Harvey (Chichester, N.Y., 1998); Quantitative Calculations In Pharmaceutical Practice And Research by T. P. Hadjiioannou (VCH, N.Y., 1993); Drug Fate And Metabolism: Methods And Techniques by E. R. Garrett and J. L. Hirtz (M. Dekker, N.Y., 1977); Behavioral Science Techniques: An Annotated Bibliography For Health Professionals by M. K. Tichy (Praeger Publishers, N.Y., 1975).

DETAILED DESCRIPTION OF THE INVENTION

I. Overview

Figure 1:
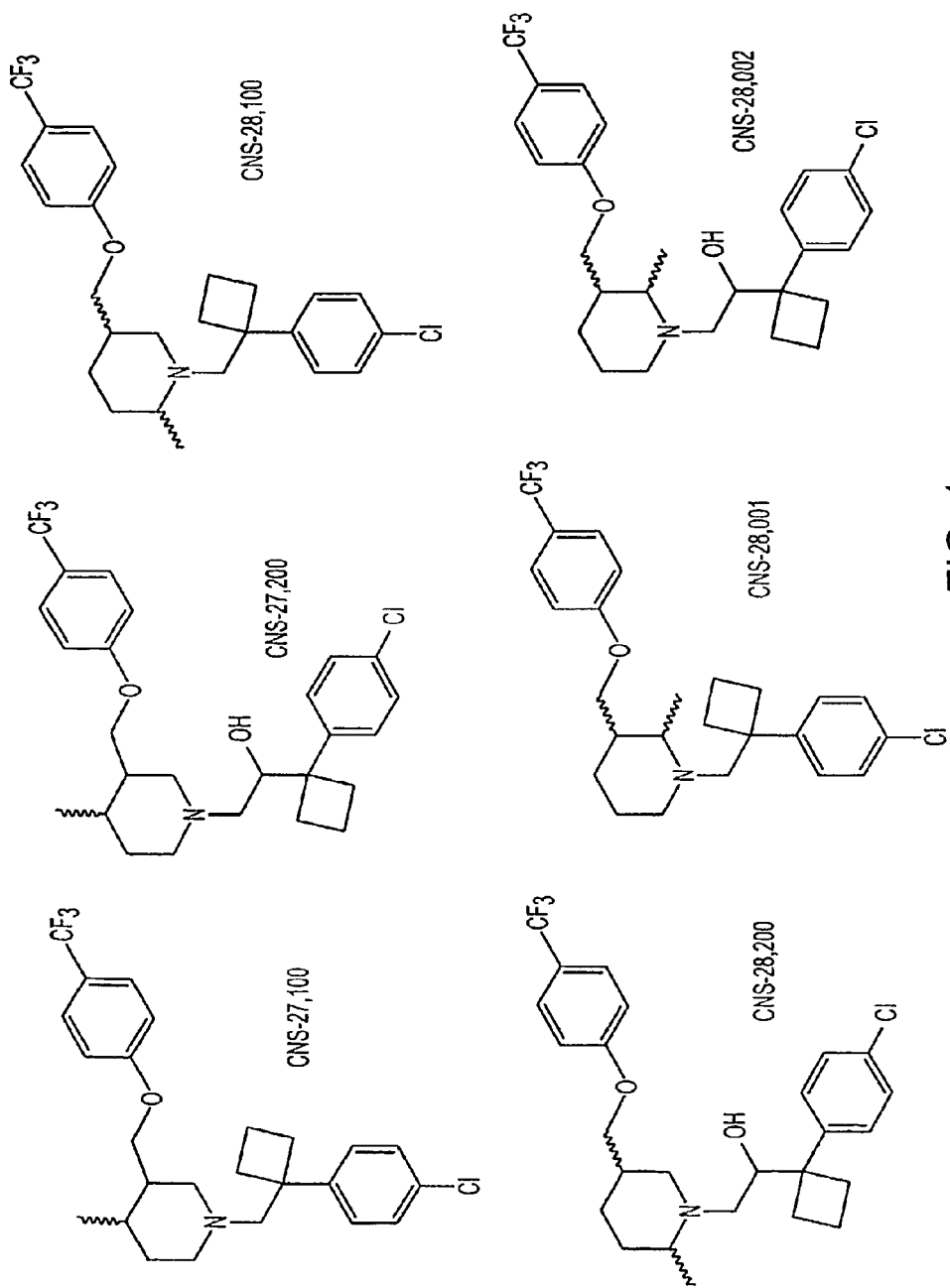
FIG. 1 shows a few illustrative dopamine transporter inhibitors, CNS-27100, CNS-27200, CNS-28100, CNS-28200, CNS-28001, and CNS-28002.

The present invention relates to the discovery of certain dopamine transporter inhibitors (collectively referred to herein as the subject "DAT inhibitors") which can be used to prevent or reduce conditions associated with a movement disorder. In certain preferred embodiments, the movement disorder is Parkinson's disease.

The subject DAT inhibitors can also be effective as part of a therapy for treating depression, sleep disorders, obesity, attention deficit disorder (ADD), attention deficit hyperactivity disorder (ADHD), certain sexual dysfunctions, and substance abuse (such as for the treatment of cocaine abuse).

One aspect of the invention features a pharmaceutical package comprising one or more of the subject DAT inhibitor(s) in an amount sufficient to treat or prevent a movement disorder in a patient, a pharmaceutically acceptable carrier, and instructions (written and/or pictorial) describing the use of the formulation for treating the patient, wherein the patient suffers from ataxia, corticobasal ganglionic degeneration (CBGD), dyskinesia, dystonia, tremors, hereditary spastic paraplegia, Huntington's disease, multiple system atrophy, myoclonus, Parkinson's disease, progressive supranuclear palsy, restless legs syndrome, Rett syndrome, spasticity, Sydenham's chorea, other choreas, athetosis, ballism, stereotypy, tardive dyskinesia/dystonia, tics, Tourette's syndrome, olivopontocerebellar atrophy (OPCA), diffuse Lewy body disease, hemibalismus, hemi-facial spasm, restless leg syndrome, Wilson's disease, stiff man syndrome, akinetic mutism, psychomotor retardation, painful legs moving toes syndrome, a gait disorder, a drug-induced movement disorder, or other movement disorder.

In certain preferred embodiments, the invention features a pharmaceutical preparation comprising one or more of the subject DAT inhibitors provided as a single oral dosage formulation in an amount sufficient to treat or prevent a movement disorder in a patient.

In other preferred embodiments, the invention features a pharmaceutical preparation comprising one or more DAT inhibitors provided in the form of a transdermal patch and formulated for sustained release of the amphetamine(s) in order to administer an amount sufficient to treat or prevent a movement disorder in a patient.

In many preferred embodiments of the packages, preparations, compositions, and methods, the invention features one or more DAT inhibitor(s) provided in an amount sufficient to treat or prevent a movement disorder in a patient by a statistically significant amount when assessed by a standardized performance test. For instance, the subject DAT inhibitor(s) are provided in an amount sufficient to treat or prevent a movement disorder in a patient by a statistically significant amount when assessed by one or more of Hoehn and Yahr Staging of Parkinson's Disease, Unified Parkinson Disease Rating Scale (UPDRS), and Schwab and England Activities of Daily Living Scale.

In certain embodiments of the packages, preparations, compositions, and methods, the invention features one or more DAT inhibitor(s) provided in an amount sufficient to treat or prevent a movement disorder in a patient by a statistically significant amount when assessed by a standardized test in combination with an empirical test selected from computer tomography (CT), magnetic resonance imaging (MRI), and positron emission tomography (PET).

Another aspect of the invention features the use of the pharmaceutical composition of DAT inhibitors in the manufacture of a medicament for prophylaxis or treatment of an animal susceptible to or suffering from ataxia, corticobasal ganglionic degeneration (CBGD), dyskinesia, dystonia, tremors, hereditary spastic paraplegia, Huntington's disease, multiple system atrophy, myoclonus, Parkinson's disease, progressive supranuclear palsy, restless legs syndrome, Rett syndrome, spasticity, Sydenham's chorea, other choreas, athetosis, ballism, stereotypy, tardive dyskinesia/dystonia, tics, Tourette's syndrome, olivopontocerebellar atrophy (OPCA), diffuse Lewy body disease, hemibalismus, hemi-facial spasm, restless leg syndrome, Wilson's disease, stiff man syndrome, akinetic mutism, psychomotor retardation, painful legs moving toes syndrome, a gait disorder, a drug-induced movement disorder, or other movement disorder, which DAT inhibitor is represented by Formula I, or a pharmaceutically acceptable salt, solvate, metabolite, or pro-drug thereof.

Another aspect of the invention relates to a method for conducting a pharmaceutical business, which includes: (a) manufacturing the packages, preparations, and compositions of the present invention; and (b) marketing to healthcare providers the benefits of using the packages, preparations, and compositions of the present invention to treat or prevent a movement disorder of treated patients.

Another aspect of the invention relates to a method for conducting a pharmaceutical business, comprising: (a) providing a distribution network for selling the packages, preparations, and compositions of the present invention; and (b) providing instruction material to patients or physicians for using the packages, preparations, and compositions of the present invention to treat or prevent a movement disorder of treated patients.

Yet another aspect of the invention relates to a method for conducting a pharmaceutical business, comprising: (a) determining an appropriate dosage of an DAT inhibitor to treat or prevent a movement disorder in a class of patients; (b) conducting therapeutic profiling of one or more formulations of the DAT inhibitor identified in step (a), for efficacy and toxicity in animals; and (c) providing a distribution network for selling the formulations identified in step (b) as having an acceptable therapeutic profile, wherein the patient suffers from ataxia, corticobasal ganglionic degeneration (CBGD), dyskinesia, dystonia, tremors, hereditary spastic paraplegia, Huntington's disease, multiple system atrophy, myoclonus, Parkinson's disease, progressive supranuclear palsy, restless legs syndrome, Rett syndrome, spasticity, Sydenham's chorea, other choreas, athetosis, ballism, stereotypy, tardive dyskinesia/dystonia, tics, Tourette's syndrome, olivopontocerebellar atrophy (OPCA), diffuse Lewy body disease, hemibalismus, hemi-facial spasm, restless leg syndrome, Wilson's disease, stiff man syndrome, akinetic mutism, psychomotor retardation, painful legs moving toes syndrome, a gait disorder, a drug-induced movement disorder, or other movement disorder.

For instance, the subject business method can include an additional step of providing a sales group for marketing the preparation to healthcare providers.

Another aspect of the invention relates to a method for conducting a medical assistance reimbursement program, comprising: (a) providing a reimbursement program which permits, for prescription of an DAT inhibitors for treating a movement order, at least partial reimbursement to a healthcare provider or patient, or payment to a drug distributor; (b) processing one or more claims for prescription of an DAT inhibitors for treating a movement order; and (c) reimbursing the healthcare provider or patient, or paying a drug distributor, at least a portion of the cost of said prescription.

Another aspect of the invention relates to a method for conducting a pharmaceutical business, comprising: (a) determining an appropriate dosage of an DAT inhibitor to treat or prevent a movement disorder function in a class of patients; and (b) licensing, to a third party, the rights for further development and sale of the DAT inhibitor for treating or preventing a movement disorder, wherein the patient suffers from ataxia, corticobasal ganglionic degeneration (CBGD), dyskinesia, dystonia, tremors, hereditary spastic paraplegia, Huntington's disease, multiple system atrophy, myoclonus, Parkinson's disease, progressive supranuclear palsy, restless legs syndrome, Rett syndrome, spasticity, Sydenham's chorea, other choreas, athetosis, ballism, stereotypy, tardive dyskinesia/dystonia, tics, Tourette's syndrome, olivopontocerebellar atrophy (OPCA), diffuse Lewy body disease, hemibalismus, hemi-facial spasm, restless leg syndrome, Wilson's disease, stiff man syndrome, akinetic mutism, psychomotor retardation, painful legs moving toes syndrome, a gait disorder, a drug-induced movement disorder, or other movement disorder.

II. Definitions

For convenience, certain terms employed in the specification, examples, and appended claims are collected here.

As used herein, the term "movement disorders" includes akinesias and akinetic-rigid syndromes, dyskinesias and medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor). Examples of "akinetic-rigid syndromes" include Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification. Examples of "dyskinesias" include tremor (including rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia). Another "movement disorder" which may be treated according to the present invention is Gilles de la Tourette's syndrome, and the symptoms thereof.

As used herein, the term "depression" includes depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, seasonal affective disorder, or bipolar disorders or manic depression, for example, bipolar I disorder, bipolar II disorder and cyclothymic disorder.

An "effective amount" of, e.g., an DAT inhibitor, with respect to the subject method of treatment, refers to an amount of the inhibitor in a pharmaceutical preparation which, when applied as part of a desired dosage regimen, brings about improved state according to clinically acceptable standards.

The term "treat," "treating," or "treatment" as used herein means to counteract a medical condition (e.g., a movement disorder) to the extent that the medical condition is improved according to clinically acceptable standard(s). For example, "to treat a movement disorder" means to improve the movement disorder or relieve symptoms of the particular movement disorder in a patient, wherein the improvement and relief are evaluated with a clinically acceptable standardized test (e.g., a patient self-assessment scale) and/or an empirical test (e.g., PET scan).

The term "amelioration" in the case of a movement disorder refers to a decrease in the abnormal involuntary movements characterizing these two types of dyskinesia, as can be determined for example, by using the Abnormal Involuntary Movement Scale (AIMS) as will be specified hereinbelow.

The term "prevent," "preventing," or "prevention" as used herein means reducing the probability/risk of developing a condition in a subject (e.g., a human), or delaying the onset of a condition in the subject, or lessening the severity of one or more symptoms of a condition (e.g., a movement disorder) that may develop in the subject, or any combination thereof.

A "patient" or "subject" to be treated by the subject method can mean either a human or non-human animal.

The term "prodrug" represents compounds which are rapidly transformed in vivo, for example, by hydrolysis in blood into the therapeutically active agents of the present invention. A common method for making a prodrug is to include selected moieties which are converted under physiologic conditions (enzymatic or nonenzymatic) to reveal the desired molecule. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

By "transdermal patch" is meant a system capable of delivery of a drug to a patient via the skin, or any suitable external surface, including mucosal membranes, such as those found inside the mouth. Such delivery systems generally comprise a flexible backing, an adhesive, and a drug-retaining matrix, the backing protecting the adhesive and matrix, and the adhesive holding the whole on the skin of the patient. On contact with the skin, the drug-retaining matrix delivers drug to the skin, the drug then passing through the skin into the patient's system.

The terms "alkenyl" and "alkynyl" refer to unsaturated aliphatic groups analogous in length and possible substitution to the alkyls described below, but that contain at least one double or triple bond respectively.

The terms "alkoxyl" or "alkoxy" as used herein refer to an alkyl group, as defined below, having an oxygen radical attached thereto. Representative alkoxy groups include methoxy, ethoxy, propyloxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where R$_8$ represents an aryl, a cycloalkyl, a cycloalkenyl, a heterocycle, or a polycycle, and m is zero or an integer in the range of 1 to 8.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 8 or fewer carbon atoms in its backbone (e.g., C1-C8 for straight chains, C3-C8 for branched chains), and more preferably 5 or fewer. Likewise, preferred cycloalkyls have from 3-10 carbon atoms in their ring structure, and more preferably have 5, 6, or 7 carbons in the ring structure.

Moreover, the term "alkyl" (or "lower alkyl") as used throughout the specification, examples, and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl, and sulfonate), and silyl groups, as well as ethers, alkylthios, carbonyls (including ketones, aldehydes, carboxylates, and esters), —$CF_3$, —CN, and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Unless the number of carbons is otherwise specified, "lower alkyl" as used herein means an alkyl group, as defined above, but having from one to eight carbons, more preferably from one to five carbon atoms, in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "aralkyl," as used herein, refers to an alkyl group substituted with an aryl group (e.g., an aromatic or heteroaromatic group).

The term "aryl" as used herein includes 5-, and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, and pyrimidine, and the like. Those aryl groups having heteroatoms in the ring structure may also be referred to as "aryl heterocycles," "heteroaryls," or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle" or "cyclic alkyl," as used herein, refers to an aromatic or non-aromatic ring in which each atom of the ring is carbon.

The term "heteroatom," as used herein, means an atom of any element other than carbon or hydrogen. Preferred heteroatoms are nitrogen, oxygen, and sulfur.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "metabolites" refers to active derivatives produced upon introduction of a compound into a biological milieu, such as a patient.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "polycyclyl" or "polycyclic group" refer to two or more rings (e.g., cycloalkyls, cycloalkenyls, cycloalkynyls, aryls, and/or heterocyclyls) in which two or more carbons are common to two adjoining rings, e.g., the rings are "fused rings." Rings that are joined through non-adjacent atoms are termed "bridged" rings. Each of the rings of the polycycle can be substituted with such substituents as described above, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P.G.M. Protective Groups in Organic Synthesis, 2nd ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the definition of each expression, e.g., alkyl, m, n, etc., when it occurs more than once in any structure, is intended to be independent of its definition elsewhere in the same structure.

Contemplated equivalents of the compounds described above include compounds which otherwise correspond thereto, and which have the same general properties thereof (e.g., the ability to affect movement disorders), wherein one or more simple variations of substituents are made which do not adversely affect the efficacy of the compound. In general, the compounds of the present invention may be prepared by the methods described below, or by modifications thereof, using readily available starting materials, reagents, and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

III. Exemplary Compounds of the Invention

The subject DAT inhibitors are represented by Formula I, or are a pharmaceutically acceptable salt, solvate, metabolite or pro-drug thereof:

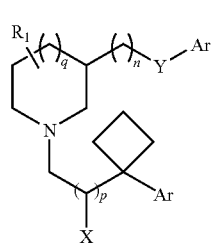

(I)

wherein, as valence and stability permit,

Ar, independently for each occurrence, represents a substituted or unsubstituted aryl or heteroaryl ring;

X represents —H or —OR;

Y represents —O—, —S—, —C(R)$_2$—, or —N(R)—;

R, independently for each occurrence, represents —H or lower alkyl;

$R_1$ represents one or more substituents to the ring to which it is attached, such as halogen, amino, acylamino, amidino, cyano, nitro, azido, ether, thioether, sulfoxido, -J-$R_2$, -J-OH, -J-lower alkyl, -J-lower alkenyl, $R_2$, -J-SH, -J-NH$_2$, or substituted or unsubstituted lower alkyl, lower alkenyl, cycloalkyl, heterocyclyl, cycloalkylalkyl, heterocyclylalkyl, aryl, heteroaryl, aralkyl, or heteroaralkyl, or protected forms of the above;

$R_2$, independently for each occurrence, represents H or substituted or unsubstituted lower alkyl, cycloalkyl, heterocyclyl, aralkyl, heteroaralkyl, aryl, or heteroaryl;

J represents, independently for each occurrence, a chain having from 0-8 (preferably from 0-4) units selected from —C(R)$_2$—, —N(R)—, —O—, and —S—;

n is an integer from 0 to 2;

p is 0 or 1; and q is an integer from 0 to 2, preferably 1.

In certain embodiments, $R_1$ comprises one or more lower alkyl groups, e.g., positioned at the 2-, 4-, and/or 6-position of the piperidine ring.

In certain embodiments, substituents on Ar (e.g., other than hydrogen) are selected from halogen, cyano, alkyl (including perfluoroalkyl), alkenyl, alkynyl, aryl, hydroxyl, alkoxy, silyloxy, amino, nitro, thiol, amino, imino, amido, phosphoryl, phosphonate, carboxyl, carboxamide, silyl, thioether, alkylsulfonyl, arylsulfonyl, sulfoxide, selenoether, ketone, aldehyde, ester, or —(CH$_2$)$_m$R$_2$, where m is an integer from 0 to 4.

In certain embodiments, non-hydrogen substituents are selected from halogen, cyano, alkyl (including perfluoroalkyl), hydroxyl, alkoxy, alkenyl, alkynyl, aryl, nitro, thiol, imino, amido, carboxyl, thioether, alkylsulfonyl, arylsulfonyl, ketone, aldehyde, and ester. In certain embodiments, non-hydrogen substituents are selected from halogen, cyano, alkyl (including perfluoroalkyl), alkenyl, alkynyl, nitro, amido, carboxyl, alkylsulfonyl, ketone, aldehyde, and ester.

In certain embodiments, substituents on Ar are located at the para position.

In certain embodiments, one or both occurrences of Ar are phenyl rings. In certain such embodiments, the phenyl rings are substituted by one or more electron-withdrawing substituents, such as halogen, cyano, nitro, perfluoroalkyl (e.g., CF$_3$, C$_2$F$_5$, etc.), acyl, etc.

Certain representative illustrative dopamine transporter inhibitors are shown in FIG. 1, including CNS-27100, CNS-27200, CNS-28100, CNS-28200, CNS-28001, and CNS-28002. These are the preferred embodiments of the DAT inhibitors. The structures of these compounds are shown below:

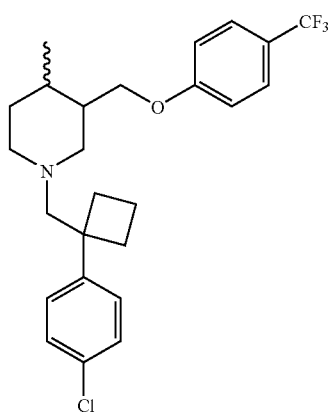

CNS-27,100

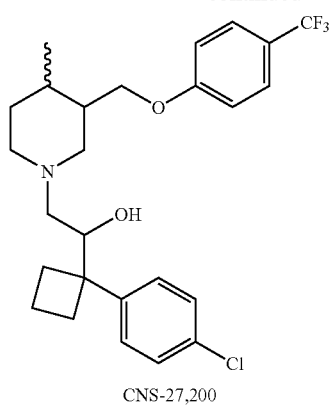
CNS-27,200
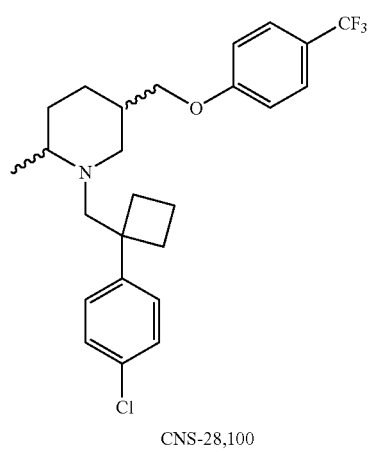
CNS-28,100
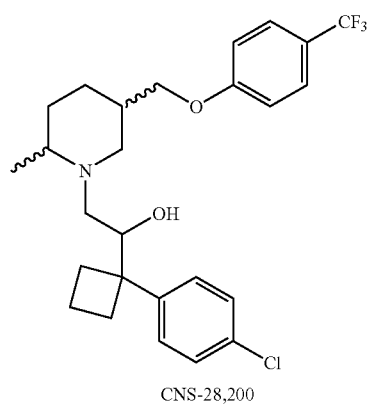
CNS-28,200
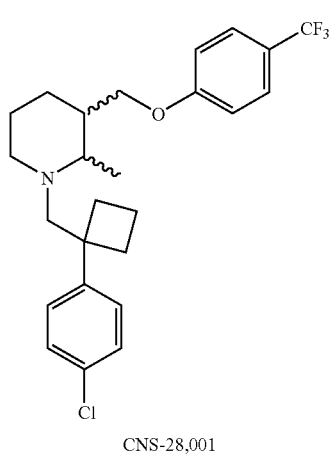
CNS-28,001
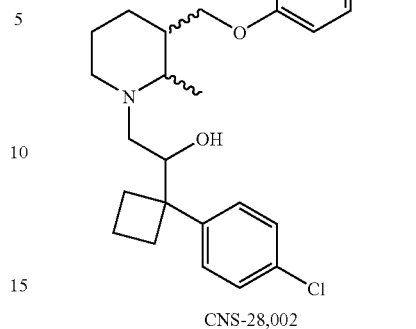
CNS-28,002
Other embodiments of the DAT inhibitors are listed below:
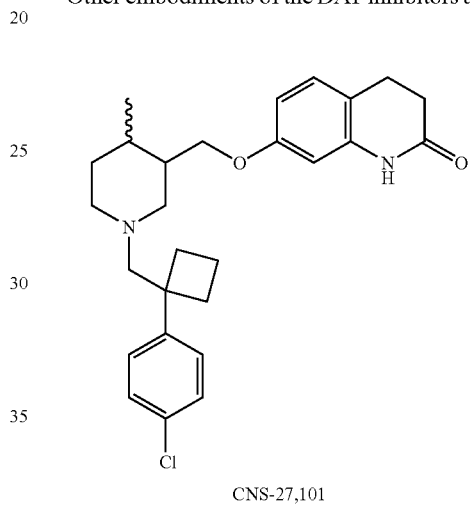
CNS-27,101
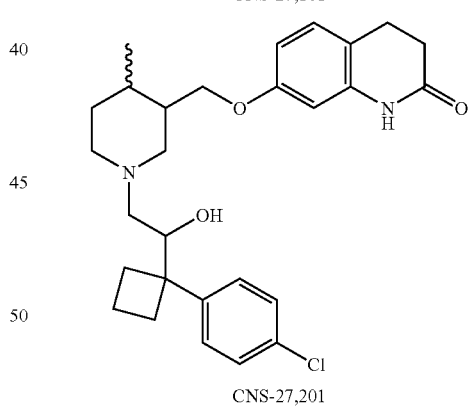
CNS-27,201

CNS-28,101

CNS-28,201

CNS-28,003

CNS-28,004

In addition to humans, other animal subjects to which the invention is applicable extend to both domestic animals and livestock, raised either as pets or for commercial purposes. Examples are dogs, cats, cattle, horses, sheep, hogs, and goats.

Still another aspect of the invention relates to the use of DAT inhibitors for lessening the severity or prophylactically preventing the occurrence of movement disorders in an animal, and thus, altering the mental or physical state of the animal.

The compounds of the present invention may also be useful for treating and/or preventing memory impairment due to a movement disorder.

In certain preferred embodiment, the movement disorder is Parkinson's disease.

A. Synthesis of DAT Inhibitors

The following section describes in detail the synthesis of several exemplary DAT inhibitors of the invention. However, these descriptions/examples are for illustrative purpose only, and should not be construed to be limiting to only the compounds described. A skilled artisan could readily synthesize other related compounds of the invention with (or without) minor modifications of the schemes described below.

Unless otherwise noted, reagents and solvents were used as received from commercial suppliers. Proton and carbon nuclear magnetic resonance spectra were obtained on a Bruker AV 400 at 400 MHz for proton and 100 MHz for carbon, or on a Bruker AMX 500 spectrometer at 500 MHz for proton and 125 MHz for carbon. Spectra are given in ppm ($\delta$). Tetramethylsilane was used as an internal standard for proton spectra and the solvent peak was used as the reference peak for carbon spectra. HPLC analyses were performed on a Waters 2695 HPLC with an Alltech Platinum C18 column (53×7 mm, 100 Å) with UV detection at 220 nm or 254 nm, using a standard solvent gradient program (Method A). Mass spectra were obtained on a Perkin Elmer Sciex API 150EX Turbo Ion Spray detector.

HPLC Method A:

Column: Alltech Platinum C18 Column, 53×7 mm, 100 Å, 3 µm;

Column temperature: 40° C.

Mobile phase A: 99.9: 0.1 Water/TFA

Mobile phase B: 99.9: 0.1 Acetonitrile/TFA

Detector: 220 nm or 254 nm

Sample preparation: Dissolve in acetonitrile or 50:50 acetonitrile/water

Injection volume: 10 µL

Gradient:

| Time (Minutes) | Flow (mL/min.) | % A | % B |
|---|---|---|---|
| 0 | 2.5 | 5 | 95 |
| 1 | 2.5 | 5 | 95 |
| 8 | 2.5 | 95 | 5 |
| 10 | 2.5 | 5 | 95 |
| 12 | 2.5 | 5 | 95 |

Collection A: Preparation of 2-Me-2

A 400-mL Fisher-Porter reactor was charged with absolute ethanol (225 mL), concentrated hydrochloric acid (13.0 g), 10% Pd/C (4.0 g) and ethyl-2-methylnicotinate (15.0 g, 90.8 mmol). The mixture was heated to 80° C. and placed under 60 psi hydrogen pressure. The mixture was then stirred for 16 hour under these conditions. The mixture was cooled and filtered. The filtrate was evaporated under reduced pressure to give a tacky solid. This solid was dissolved in water (25 mL) and the pH was adjusted to pH 8.2 using saturated sodium bicarbonate. The solution was freeze-dried to give 2-Me-2 (12.6 g, 81%). The $^1$H NMR spectrum was consistent with the assigned structure.

Collection A: Preparation of 2-Me-4

A 1-L, three-neck, round-bottomed flask, fitted with a mechanical stirrer and placed under an argon atmosphere, was charged with 2-Me-2 (10.5 g, 51.0 mmol) and methylene chloride (630 mL). While stirring at ambient temperature, triethylamine (22.7 g, 224 mmol) was added. Next, 1-(4-chlorophenyl)-cyclobutanecarboxylic acid (17.2 g, 82.0 mmol) was added, followed by bromotris(pyrrolidino)phosphonium hexafluorophosphate ("PyBroP," 39.2 g, 84.0 mmol). The mixture was stirred under argon at ambient temperature for 16 h. A solution of 10% potassium hydroxide (700 mL) was added to the reaction mixture. Ethyl acetate (350 mL) was then added and the mixture was stirred for 5 min. The layers were separated and the aqueous layer was re-extracted with ethyl acetate (300 mL). The ethyl acetate extracts were combined and dried over anhydrous magnesium sulfate. This mixture was filtered and the filtrate was evaporated under reduced pressure to give crude product (57.2 g). The crude product was split in two equal portions. Each portion was placed on a 100 mm diameter flash column, packed with silica gel (750 g) using 60:30:1 chloroform/ethyl acetate/MeOH. Each column was eluted with 60:30:1 chloroform/ethyl acetate/MeOH. The fractions containing the purest product were combined and the solvents evaporated to dryness under reduced pressure. After column chromatography, purified 2-Me-4 (17.8 g) was isolated in two lots: (9.4 g, 50.5%), HPLC (Method A) 58.1% (AUC), $t_R$=6.11 min (see Attachment 2); and (8.7 g, 46.9%), HPLC (Method A) 76.5% (AUC), $t_R$=6.10 min.

Collection A: Preparation of 2-Me-5

A 1-L, three-neck, round-bottomed flask placed under argon was charged with tetrahydrofuran (210 mL), then was cooled to 0° C. Lithium aluminum hydride (27.9 g) was added slowly at 0° C. In a separate flask, 2-Me-4 (8.2 g, 22.5 mmol) was dissolved in tetrahydrofuran (150 mL). This solution of 2-Me-4 was added to the cold slurry at 0° C. Additional tetrahydrofuran (50 mL) was added to rinse in residues. The mixture was stirred for 16 h under argon, allowing the mixture to warm to ambient temperature. The mixture was cooled to 0° C. and water (200 mL) was cautiously added. Next, 15% sulfuric acid was added, which dropped the pH to pH 3.3. Saturated sodium bicarbonate was added to adjust pH to pH 8.0. The solids were filtered through paper in a Buchner funnel in portions (very sluggish). The filter-cake was washed with ethyl acetate (1×500 mL, 2×800 mL). These washes were each used to re-extract the aqueous layer. The ethyl acetate extracts were combined and dried over anhydrous magnesium sulfate, then the mixture was filtered. The filtrate was evaporated under reduced pressure to give a crude product (6.1 g). The crude product was combined with other crops (7.1 g) and placed on a 100 mm diameter flash column, packed with silica gel (800 g) using 60:30:1 chloroform/ethyl acetate/meOH. The column was eluted with 60:30:1 chloroform/ethyl acetate/meOH. The fractions containing the purest product were combined and the solvents evaporated to dryness under reduced pressure to give purified 2-Me-5 (3.4 g, 22.5%): HPLC (Method A) 92.8% (AUC), $t_R$=4.79 min.

Collection A: Preparation of 2-Me-5 Mesylate Intermediate

A 100-mL, one-neck, round-bottomed flask was charged with 2-Me-5 (3.4 g, 11.0 mmol) and methylene chloride (47 mL). Next, diisopropylethylamine (3.6 g, 27.6 mmol) was added to the flask, followed by the addition of mesyl chloride (1.4 g, 12.2 mmol). The reaction mixture had warmed to a gentle reflux. The mixture was stirred for 1 h, while it cooled toward ambient temperature. The reaction mixture was evaporated to dryness under reduced pressure to give crude product (7.3 g). The crude product was placed on a 40 mm diameter flash column, packed with silica gel (185 g) using 230:30:3 chloroform/ethyl acetate/2 M ammonia in methanol The column was eluted with 230:30:3 chloroform/ethyl acetate/2 M ammonia in methanol. The fractions containing the purest product were combined and the solvents evaporated to dryness under reduced pressure to give purified 2-Me-5 mesylate intermediate (3.4 g, 79.8%): HPLC (Method A) 98.8% (AUC), $t_R$=5.15 min.

Collection A: Preparation of 2-Me-6

A 200-mL, one-neck, round-bottomed flask was charged with 2-Me-5 mesylate intermediate (3.4 g, 8.8 mmol and dimethylformamide (50 mL). To the reaction mixture, α,α,α-trifluoro-p-cresol (1.4 g, 8.8 mmol) was added, followed by cesium carbonate (7.2 g, 22.1 mmol). The mixture was stirred in a preheated oil bath (75° C.) for 4 h, then was stirred for 16 h with no heating, while cooling toward ambient temperature. Ethyl acetate (140 mL) was added and the mixture was washed with brine (3×100 mL). The ethyl acetate layer was dried over anhydrous magnesium sulfate, then filtered. The filtrate was evaporated under reduced pressure to dryness to give a crude product (4.0 g). The crude product was placed on a 40 mm diameter flash column, packed with silica gel (220 g) using 460:60:3 chloroform/ethyl acetate/2 M ammonia in methanol. The column was eluted with 460:60:3 chloroform/ethyl acetate/2 M ammonia in methanol. The fractions containing the purest product were combined and the solvents evaporated to dryness under reduced pressure to give purified 2Me-6 (2.1 g, 52.5%): LC/MS (Ion spray) m/z 452 $[C_{25}H_{29}ClF_3NO+H]^+$, HPLC (Method A)>99% (AUC), $t_R$=6.56 min. The $^1$H NMR and $^{13}$C NMR spectra were consistent with the assigned structure.

Collection A: Preparation of 4-Me-1

A 500-mL, three-neck, round-bottomed flask was charged with 4-methylnicotinic acid hydrochloride (7.4 g, 42.8 mmol) and hydrochloric acid in methanol (200 mL; 200 mg/mL). The mixture was heated at a gentle reflux for 5 h, then it was stirred for 16 h, while cooling to ambient temperature. An in-process HPLC was run after stirring for 15 h at ambient temperature [HPLC (Method A): 95.0% (AUC), $t_R$=1.84 min]. The solution was evaporated under reduced pressure to dryness to give 4-Me-1 (10.9 g, quantitative).

Collection A: Preparation of 4-Me-2

A 400-mL Fisher-Porter reactor was charged with methanol (115 mL), concentrated hydrochloric acid (4.8 g), 10% Pd/C (1.5 g) and 4-Me-1 (10.9 g, 42.8 mmol). The mixture was heated to 80° C. and placed under 60 psi hydrogen pressure. The mixture was then stirred for 16 h under these conditions. The mixture was cooled and filtered through a bed of diatomaceous earth. The filtrate was evaporated under reduced pressure to give 4-Me-2 (9.6 g, quantitative). The $^1$H NMR spectrum was consistent with the assigned structure.

Collection A: Preparation of 4-Me-4

A 2-L, three-neck, round-bottomed flask, fitted with a mechanical stirrer and placed under an argon atmosphere, was charged with 4-Me-2 (9.6 g, 42.8 mmol) and methylene chloride (535 mL). While stirring at ambient temperature, triethylamine (19.1 g, 188 mmol) was added. Next, 1-(4-chlorophenyl)-cyclobutanecarboxylic acid (14.5 g, 68.8 mmol) was added, followed by bromotris(pyrrolidino)phosphonium hexafluorophosphate (PyBroP, 32.9 g, 70.5 mmol). The mixture was stirred under argon at ambient temperature for 16 h. A solution of 10% potassium hydroxide (650 mL) was added to the reaction mixture. Ethyl acetate (400 mL) was then added and the mixture was stirred for 5 min. The layers were separated and the aqueous layer was re-extracted with ethyl acetate (400 mL). The ethyl acetate extracts were combined and dried over anhydrous magnesium sulfate. This mixture was filtered and the filtrate was evaporated under reduced pressure to give crude product (47.1 g). The crude product was split in two equal portions. The first portion was placed on a 100 mm diameter flash column, packed with silica gel (700 g) using 60:30:1 $CHCl_3$/EtOAc/MeOH This column was eluted with 60:30:1 $CHCl_3$/EtOAc/MeOH. The second portion was placed on a 100 mm diameter flash column, packed with silica gel (700 g) using 160:40:1 $CHCl_3$/EtOAc/MeOH. This column was eluted with 160:40:1 $CHCl_3$/EtOAc/MeOH. The fractions containing the purest product were combined and the solvents evaporated to dryness under reduced pressure. Less pure fractions were combined and the solvents evaporated under reduced pressure to give material (3.2 g) for a third smaller column. After column chromatography, purified 4-Me-4 (11.4 g) was isolated in three lots: (9.4 g, 35.4%), HPLC (Method A) 83.8% (AUC), $t_R$=5.90 min. (4.5 g, 30.2%), HPLC (Method A) 93.4% (AUC), $t_R$=5.88 min; and (1.6 g, 10.4%).

Collection A: Preparation of 4-Me-5

A 2-L, three-neck, round-bottomed flask placed under argon was charged with tetrahydrofuran (300 mL), then was cooled to 0° C. Lithium aluminum hydride (38.7 g) was added slowly at 0° C. In a separate flask, 4-Me-4 (11.4 g) in three lots (5.3 g, 15.1 mmol; 4.5 g, 12.9 mmol; and 1.6 g, 4.4 mmol) was dissolved in tetrahydrofuran (250 mL). The solution of 4-Me-4 was added to the cold slurry of LAH at 0° C. Additional tetrahydrofuran (25 mL) was added to rinse in residues. The mixture was stirred for 16 h under argon, allowing the mixture to warm to ambient temperature. The mixture was cooled to 0° C. and water (300 mL) was cautiously added. Next, 15% sulfuric acid was added, which dropped the pH to pH 3.5. Solid sodium bicarbonate was added to adjust pH to pH 7.6. The solids were filtered through diatomaceous earth/paper in a Buchner funnel in portions (very sluggish). The filter cake was washed with ethyl acetate (1×250 mL, 2×400 mL). These washes were each used to re-extract the aqueous layer. The ethyl acetate extracts were combined and dried over anhydrous magnesium sulfate, then the mixture was filtered. The filtrate was evaporated under reduced pressure to give a crude product (8.1 g). The crude product was placed on a 100 mm diameter flash column, packed with silica gel (800 g) using 160:40:1 $CHCl_3$/EtOAc/MeOH. The column was eluted with 60:30:1 $CHCl_3$/EtOAc/MeOH. The fractions containing the purest product were combined and the solvents evaporated to dryness under reduced pressure to give purified 4-Me-5 (2.8 g, 28.1%): HPLC (Method A) 77.6% (AUC), $t_R$=5.13 min.

Collection A: Preparation of 4-Me-5 Mesylate Intermediate

A 100-mL, one-neck, round-bottomed flask was charged with 4-Me-5 (2.8 g, 9.1 mmol) and methylene chloride (40 mL). Next; diisopropylethylainine (2.9 g, 22.7 mmol) was added to the flask, followed by the addition of mesyl chloride (1.2 g, 10.0 mmol). The reaction mixture had warmed to a gentle reflux. The mixture was stirred for 1 h, while it cooled toward ambient temperature. The reaction mixture was evaporated to dryness under reduced pressure to give crude product (5.7 g). The crude product was placed on a 40 mm diameter flash column, packed with silica gel (200 g) using 230:30:3 chloroform/ethyl acetate/2 M ammonia in MeOH. The column was eluted with 230:30:3 chloroform/ethyl acetate/2 M ammonia in MeOH. The fractions containing the purest product were combined and the solvents evaporated to dryness under reduced pressure to give purified 4-Me-5 mesylate intermediate (2.2 g, 62.7%): HPLC (Method A) 91.6% (AUC), $t_R$=5.26 min.

Collection A: Preparation of 4-Me-6

A 200-mL, one-neck, round-bottomed flask was charged with 4-Me-5 mesylate intermediate (2.2 g, 5.7 mmol) and dimethylformamide (35 mL). To the reaction mixture, α,α,α-trifluoro-p-cresol-(0.9 g, 5.7 mmol) was added, followed by cesium carbonate (4.7 g, 14.3 mmol). The mixture was stirred in a preheated oil bath (75° C.) for 5 h, then was stirred for 16 h with no heating while cooling toward ambient temperature. Ethyl acetate (100 mL) was added and the mixture was washed with brine (3×70 mL). The ethyl acetate layer was dried over anhydrous magnesium sulfate, then filtered. The filtrate was evaporated under reduced pressure to dryness to give a crude product (3.8 g). The crude product was placed on a 40 mm diameter flash column, packed with silica gel (215 g) using 460:60:3 chloroform/ethyl acetate/2 M ammonia in methanol. The column was eluted with 460:60:3 chloroform/ethyl acetate/2 M ammonia in methanol. The fractions containing the purest product were combined and the solvents evaporated to dryness under reduced pressure to give purified 4-Me-6 (1.1 g, 43.1%): LC/MS (Ion spray) m/z 452 $[C_{25}H_{29}ClF_3NO+H]^+$; HPLC (Method A) 93.8% (AUC), $t_R$=6.64 min. The $^1H$ NMR and $^{13}C$ NMR spectra were consistent with the assigned structure.

Collection A: Preparation of 6-Me-2

A 400-mL Fisher-Porter reactor was charged with methanol (300 mL), concentrated hydrochloric acid (13.0 g), 10% Pd/C (4.0 g) and methyl-6-methylnicotinate (20.0 g, 132 mmol). The mixture was heated to 80° C. and placed under 60 psi hydrogen pressure. The mixture was then stirred for 21 h under these conditions. The mixture was cooled and filtered. The filtrate was evaporated under reduced pressure to give 6-Me-2 (27.0 g, quantitative). The $^1H$ NMR spectrum was consistent with the assigned structure.

Collection A: Preparation of 6-Me-4

A 2-L, three-neck, round-bottomed flask, fitted with a mechanical stirrer and placed under an argon atmosphere, was charged with 6-Me-2 (14.0 g, 72.3 mmol) and methylene chloride (900 mL). While stirring at ambient temperature, triethylamine (32.2 g, 318 mmol) was added. Next, 1-(4-chlorophenyl)-cyclobutanecarboxylic acid (24.5 g, 116.2 mmol) was added, followed by bromotris(pyrrolidino)phosphonium hexafluorophosphate (PyBroP, 55.5 g, 119.1 mmol). The mixture was stirred under argon at ambient temperature for 16 h. A solution of 10% potassium hydroxide (1.0 L) was added to the reaction mixture. Ethyl acetate (500 mL) was then added and the mixture was stirred for 5 min. The layers were separated and the aqueous layer was re-extracted with ethyl acetate (500 mL). The ethyl acetate extracts were combined and dried over anhydrous magnesium sulfate. This mixture was filtered and the filtrate was evaporated under reduced pressure to give crude product (74.3 g). The crude product was split in two equal portions. Each portion was placed on a 100 mm diameter flash column, packed with silica gel (800 g) using 60:30:1 $CHCl_3$/EtOAc/MeOH. Each column was eluted with 60:30:1 $CHCl_3$/EtOAc/MeOH. The fractions containing the purest product were combined and the solvents evaporated to dryness under reduced pressure. Less pure fractions were combined and the solvents evaporated under reduced pressure to give material (8.0 g) for a third smaller column. After column chromatography, purified 6-Me-4 (17.8 g) was isolated in three lots: (7.5 g, 29.7%), HPLC (Method A) 82.0% (AUC), $t_R$=5.83 min.; (7.4 g, 29.3%), HPLC (Method A) 78.3% (AUC), $t_R$=5.83 min.; (2.9 g, 11.5%), HPLC (Method A) 80.0% (AUC), $t_R$=5.82 min.

Collection A: Preparation of 6-Me-5

A 3-L, three-neck, round-bottomed flask placed under argon was charged with tetrahydrofuran (450 mL), then was cooled to 0° C. Lithium aluminum hydride (60.6 g) was added slowly at 0° C. In a separate flask, 6-Me-4 (17.8 g) from three lots (7.5 g, 21.4 mmol; 7.4 g, 21.2 mmol; 2.9 g, 8.3 mmol) was dissolved in tetrahydrofuran (400 mL). This solution of 6-Me-4 was added to the cold slurry of LAH at 0° C. Additional tetrahydrofuran (50 mL) was added to rinse in residues. The mixture was stirred for 16 h under argon, allowing the mixture to warm to ambient temperature. The mixture was cooled to 0° C. and water (350 mL) was cautiously added. Next, 1 N sulfuric acid (350 mL) was added, which dropped the pH to pH 7.7. The solids were filtered through paper in a Buchner funnel in portions (very sluggish). Additional water (800 mL) and ethyl acetate (400 mL) were added, to facilitate stirring. The filter cakes were each washed with ethyl acetate (1×100 mL). These washes were each used to re-extract the aqueous layer. The ethyl acetate extracts were combined and dried over anhydrous magnesium sulfate, then the mixture was filtered. The filtrate was evaporated under reduced pressure to give a crude product (13.7 g). The crude product was placed on a 100 mm diameter flash column, packed with silica gel (800 g) using 60:30:1 $CHCl_3$/EtOAc/MeOH. The column was eluted with 60:30:1 $CHCl_3$/EtOAc/MeOH. The fractions containing the purest product were combined and the solvents evaporated to dryness under reduced pressure to give purified 6-Me-5 (4.2 g) in three lots: (1.7 g, 10.7%), HPLC (Method A) 86.6% (AUC), $t_R$=4.88 min.; (1.9 g, 12.2%), HPLC (Method A) 85.4% (AUC), $t_R$=4.92 min.; and (0.6 g, 3.8%), HPLC (Method A) 81.3% (AUC), $t_R$=4.83 min.

Collection A: Preparation of 6-Me-5 Mesylate Intermediate

A 200-mL, one-neck, round-bottomed flask was charged with 6-Me-5 (4.2 g) from three lots (1.7 g, 5.5 mmol); 1.9 g, 6.2 mmol; and 0.6 g, 1.9 mmol) and methylene chloride (70 mL). Next, diisopropylethylamine (4.4 g, 33.8 mmol) was added to the flask, followed by the addition of mesyl chloride (1.7 g, 14.9 mmol). The reaction mixture had warmed to a gentle reflux. The mixture was stirred for 1 h, while it cooled toward ambient temperature. The reaction mixture was evaporated to dryness under reduced pressure to give crude product (8.5 g). The crude product was placed on a 40 mm diameter flash column, packed with silica gel (230 g) using 230:30:2 chloroform/ethyl acetate/2 M ammonia in MeOH. The column was eluted with 230:30:2 chloroform/ethyl acetate/2 M ammonia in MeOH. The fractions containing the purest product were combined and the solvents evaporated to dryness under reduced pressure to give purified 6-Me-5 mesylate intermediate (2.4 g, 45.2%): HPLC (Method A) 87.2% (AUC), $t_R$=5.17 min.

Collection A: Preparation of 6-Me-6

A 100-mL, one-neck, round-bottomed flask was charged with 6-Me-5 mesylate intermediate (2.4 g, 6.1 mmol) and dimethylformamide (38 mL). To the reaction mixture, α,α,α-trifluoro-p-cresol (1.0 g, 6.1 mmol) was added, followed by cesium carbonate (5.0 g, 15.3 mmol). The mixture was stirred in a preheated oil bath (75° C.) for 4 h, then was stirred for 16 h with no heating, while cooling toward ambient temperature. Ethyl acetate (100 mL) was added and the mixture was washed with brine (3×70 mL). The ethyl acetate liquors were dried over anhydrous magnesium sulfate, then filtered. The filtrate was evaporated under reduced pressure to dryness to give a crude product (3.9 g). The crude product was placed on a 40 mm diameter flash column, packed with silica gel (230 g) using chloroform (460 parts), ethyl acetate (60 parts) and 2M ammonia in methanol (3 parts). The column was eluted with a solvent mixture of chloroform (460 parts), ethyl acetate (60 parts) and 2M ammonia in methanol (3 parts). The fractions containing the purest product were combined and the solvents evaporated to dryness under reduced pressure to give purified 6-Me-6 (2.1 g, 76.2%). LC/MS (Ion spray) m/z 452 $[C_{25}H_{29}ClF_3NO+H]^+$. HPLC (Method A) 96.3% (AUC), $t_R$=6.41 min. The $^1$H NMR and $^{13}$C NMR spectra were consistent with the assigned structure.

Collection B: Preparation of 6-Me-2

A 400-mL, Fisher-Porter reactor was charged with methanol (300 mL), concentrated hydrochloric acid (13.0 g), 10% Pd/C (4.0 g) and methyl-6-methylnicotinate (20.0 g, 132 mmol). The mixture was heated to 80° C. and placed under 60 psi hydrogen pressure. The mixture was then stirred for 21 h under these conditions. The mixture was cooled and filtered. The filtrate was evaporated under reduced pressure to give 6-Me-2 (27.0 g, quantitative). The $^1$H NMR spectrum was consistent with the assigned structure.

Collection B: Preparation of 6-Me-3

A 250-mL, four-neck, round-bottomed flask, fitted with a magnetic stirrer was charged with 6-Me-2 (13.3 g, 68.4 mmol), tetrahydrofuran (60 mL), water (60 mL) and sodium bicarbonate (14.4 g, 171 mmol). The reaction mixture was cooled to 5° C. While keeping the pH between pH 8 to pH 9, benzylchloroformate (12.0 g, 70.4 mmol) was added slowly over 90 min. The mixture was stirred at ambient temperature for 1 h. The reaction mixture was placed under reduced pressure to remove most of the tetrahydrofuran. Ethyl acetate (50 mL) was then added and the mixture was stirred for 5 min. The layers were separated and the organic layer was washed with water (20 mL). The ethyl acetate layer was dried over anhydrous magnesium sulfate. This mixture was filtered and the filtrate was evaporated under reduced pressure to give crude product (16.5 g). The crude product was split in two equal portions. One portion was placed on a 40 mm diameter flash column, packed with silica gel (225 g) using 230:30:3 $CHCl_3$/EtOAc/MeOH. The column was eluted with 230:30:3 $CHCl_3$/EtOAc/MeOH. The fractions containing the purest product were combined and the solvents evaporated to dryness under reduced pressure. Other fractions were combined and the solvents evaporated under reduced pressure to dryness as a minor product (possible separation of diastereomers). After column chromatography, there were two products: 6-Me-3 (major product), (3.4 g, 16.8%), HPLC (Method A) 94.0% (AUC), $t_R$=5.43 min.; and 6-Me-3 (minor product), (0.4 g, 2.0%), HPLC (Method A) 98.1% (AUC), $t_R$=5.28 min.

Collection B: Preparation of 6-Me-3 Acid

A 100-mL, one-neck, round-bottomed flask was charged with tetrahydrofuran (15 mL), water (30 mL), lithium hydroxide (0.35 g, 14.6 mmol) and 6-Me-3 (3.25 g, 11.2 mmol). The mixture was stirred at ambient temperature for 16 hours. The mixture was treated with HCl to adjust the pH to pH 2.7. The liquors were extracted with ethyl acetate (2×50 mL). The ethyl acetate extracts were combined and dried over anhydrous magnesium sulfate, then the mixture was filtered. The filtrate was evaporated under reduced pressure to give a 6-Me-3 acid (3.0 g, 95.5%): HPLC (Method A) 90.7% (AUC), $t_R$=4.78 min.

Collection B: Preparation of 6-Me-4

A 50-mL, one-neck, round-bottomed flask under argon was charged with 6-Me-3 acid (2.9 g, 10.5 mmol) and tetrahydrofuran (15 mL). Next, 5.0 M borane-methyl sulfide (2.32 mL, 11.6 mmol) was added slowly to the flask over 45 min., initially at ambient temperature. As the addition progressed, the mixture was heated to a gentle reflux and this was maintained during the remainder of the addition. After the addition, the mixture was refluxed for 30 min. The mixture was then stirred for 18 hour under inert atmosphere, while cooling to ambient temperature. The reaction mixture was added slowly to cold (5° C.) methanol (35 mL). Gas evolution was seen. The reaction mixture was evaporated to dryness under reduced pressure to give 6-Me-4 (2.7 g, 97.6%): HPLC (Method A) 89.9% (AUC), $t_R$=4.87 min.

Collection B: Preparation of SC-2

A 200-mL, one-neck, round-bottomed flask under argon was charged with 1-(4-chlorophenyl)-1-cyclobutanecarbonitrile (10.0 g, 52.2 mmol) and dry toluene (60 mL). To the reaction mixture, 3.0 M methylmagnesium bromide (52.2 mL, 157 mmol) was added slowly over 20 min. The mixture was heated to 95° C. for 12 hours. A solution of 6 N HCl (40 mL) was added to the mixture (gas evolution seen, exothermic). The mixture was heated at reflux for 60 min., then cooled to ambient temperature. The liquors were extracted with ethyl acetate (2×400 mL). The ethyl acetate extracts were combined and washed with brine (80 mL). The ethyl acetate liquors were dried over anhydrous magnesium sulfate, then filtered. The filtrate was evaporated under reduced pressure to dryness to give SC-2 (11.1 g, quantitative): HPLC (Method A) 97.3% (AUC), $t_R$=5.64 min.

Collection B: Preparation of SC-3

A 100-mL, one-neck, round-bottomed flask under argon was charged with SC-2 (11.0 g, 52.7 mmol) and methylene chloride (40 mL). The mixture was cooled to 20° C., then liquid bromine (8.4 g, 52.7 mmol) was added slowly over 20 min. The mixture was stirred at ambient temperature for 30 min., then was poured over ice water (55 g). The liquors were separated and the aqueous layer was re-extracted with methylene chloride (20 mL). The methylene chloride extracts were combined and were dried over anhydrous magnesium sulfate, then filtered. The filtrate was evaporated under reduced pressure to dryness to give SC-3 (14.5 g, 95.3%): HPLC (Method A) 71.2% (AUC), $t_R$=5.88 min.

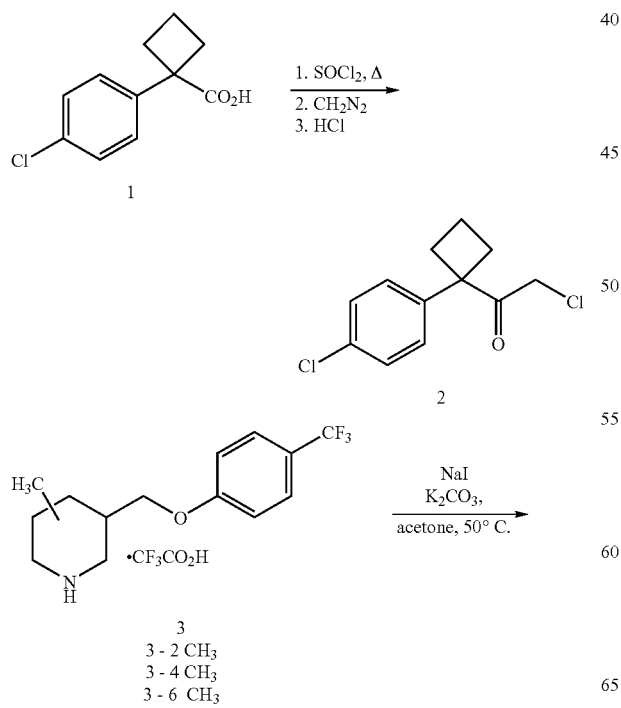

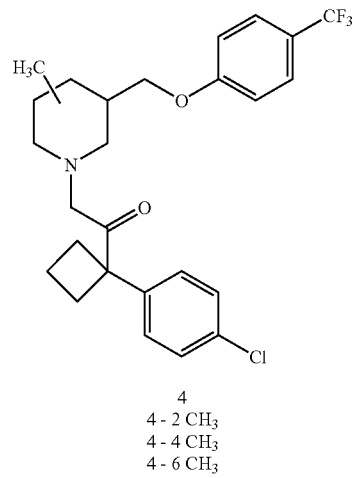

4
4 - 2 $CH_3$
4 - 4 $CH_3$
4 - 6 $CH_3$

A mixture of 1 (0.942 g, 4.48 mmol) and thionyl chloride (2 mL) were heated at reflux for 3 hours. The reaction mixture was concentrated, diluted with THF (2 mL), and concentrated in vacuo to give an oil. The oil was dissolved in THF (15 mL) and then cooled to 0° C. Next, diazomethane (generated at 0° C. from 2 g 1-methyl-3-nitro-1-nitrososguanidine in 15 mL diethyl ether and 1.36 g sodium hydroxide in 15 mL water) was added. The resulting solution was maintained at 0° C. overnight. Hydrochloric acid (5 mL; 4 M) was carefully added. The reaction mixture was maintained at 0° C. for 1 hour, and then concentrated to an oil. The oil was purified by column chromatography on silica gel eluting with hexane/ethyl acetate (90:10) to give 2 as a colorless oil.

To a solution of 2 (96 mg, 0.393 mmol) in acetone (0.5 mL) was added sodium iodide (59 mg, 0.393 mmol). After 5 minutes at room temperature, the mixture was added to a mixture of 3 (127 mg, 0.328 mmol) and potassium carbonate (226 mg) in acetone (0.5 mL). The resulting mixture was heated to 50° C. for 18 hours. The reaction mixture was poured into water (20 mL) and extracted with ethyl acetate (2×20 mL). The organic extracts were combined, washed with brine (15 mL), dried over anhydrous sodium sulfate, filtered, and concentrated to a yellow oil. The oil was purified by column chromatography on silica gel eluting with hexane/ethyl acetate/2 N ammonia in ethanol (80:16:4) to give 4 as a colorless oil.

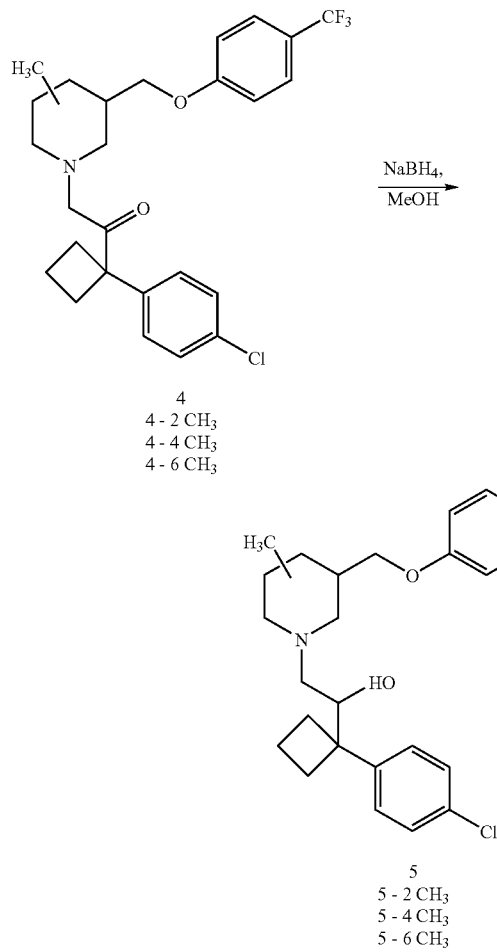

4
4 - 2 CH₃
4 - 4 CH₃
4 - 6 CH₃

5
5 - 2 CH₃
5 - 4 CH₃
5 - 6 CH₃

To a solution of 4 (67.5 mg, 0.141 mmol) in methanol (1 mL) at 0° C. was added sodium borohydride (11 mg, 0.282 mmol). The reaction mixture was maintained at room temperature for 2 hours. The reaction mixture was poured into water (10 mL) and extracted with ethyl acetate (2×15 mL). The organic extracts were combined, washed with brine (10 mL), dried over anhydrous sodium sulfate, filtered, and concentrated to a colorless oil. The oil was purified by column chromatography on silica gel eluting with hexane/ethyl acetate/2 N ammonia in ethanol (80:16:4) to give 5 as a colorless oil.

Other compounds of similar structure can be synthesized with minor modification.

B. Combinations Including DAT Inhibitors

In certain embodiments, the method includes administering, conjointly with the pharmaceutical preparation, one or more of physical therapy, occupational therapy, or speech/language therapy.

An agent to be administered conjointly with a subject compound may be formulated together with a subject compound as a single pharmaceutical preparation, e.g., as a pill or other medicament including both agents, or may be administered as a separate pharmaceutical preparation.

In certain embodiments of the packages, preparations, compositions, and methods for the treatment of a movement disorder, the invention further comprises one or more therapeutic agents for treating Parkinson's disease selected from a dopamine precursor, such as L-dopa; a dopaminergic agent, such as Levodopa-carbidopa (Sinemet®, Sinemet CR®) or Levodopa-benzerazide (Prolopa®, Madopar®, Madopar HBS®); a dopaminergic and anti-cholinergic agent, such as amantadine (Symmetryl®, Symadine®); an anti-cholinergic agent, such as trihexyphenidyl (Artane®), benztropine (Cogentin®), ethoproprazine (Parsitan®), or procyclidine (Kemadrin®); a dopamine agonist, such as apomorphine, bromocriptine (Parlodel®), cabergoline (Dostinex®), lisuride (Dopergine®), pergolide (Permax®), pramipexole (Mirapex®), or ropinirole (Requip®); a MAO-B (monoamine oxidase B) inhibitor, such as selegiline or deprenyl (Atapryl®, Carbex®, Eldepryl®); a COMT (catechol O-methyl-transferase) inhibitor, such as tolcapone (Tasmar®) or entacapone (Comtan®); or other therapeutic agents, such as baclofen (Lioresal®), domperidone (Motilium®), fludrocortisone (Florinef®), midodrine (Amatine®), oxybutinin (Ditropan®), propranolol (Inderal®, Inderal-LA®), clonazepam (Rivotril®), or yohimbine.

In certain embodiments of the packages, preparations, compositions, and methods for the treatment of a movement disorder, the invention further comprises one or more therapeutic agents for treating dystonia selected from an anti-cholinergic agent, such as trihexyphenidyl (Artane®), benztropine (Cogentin®), ethoproprazine (Parsitan®), or procyclidine (Kemadrin®); a dopaminergic agent, such as Levodopa-carbidopa (Sinemet®, Sinemet CR®) or Levodopa-benzerazide (Prolopa®, Madopar®, Madopar HBS®); a muscle relaxant, such as baclofen (Lioresal®); a sedative, such as Clonazepam (Rivotril®); an anticonvulsant agent, such as carbamazepine (Tegretol®); a dopamine reuptake inhibitor, such as tetrabenazine (Nitoman®); or a dopamine blocker, such as haloperidol (Haldol®).

In certain embodiments of the packages, preparations, compositions, and methods for the treatment of a movement disorder, the invention further comprises one or more therapeutic agents for treating tremor selected from a β-blocker, such as propranolol (Inderal®, Inderal-LA®); an anticonvulsant agent, such as primidone (Mysoline®); or a carbonic anhydrase inhibitor, such as acetalzolamide (Diamox®) or methazolamide (Neptazane®).

In certain embodiments of the packages, preparations, compositions, and methods for the treatment of a movement disorder, the invention further comprises one or more therapeutic agents for treating myoclonus selected from a sedative, such as clonazepam (Rivotril®); or an anticonvulsant agent, such as valproic acid (Epival®).

In certain embodiments of the packages, preparations, compositions, and methods for the treatment of a movement disorder, the invention further comprises one or more therapeutic agents for treating chorea selected from a dopamine blocker, such as haloperidol (Haldol®); or a dopamine reuptake inhibitor, such as tetrabenazine (Nitoman®).

In certain embodiments of the packages, preparations, compositions, and methods for the treatment of a movement disorder, the invention further comprises one or more therapeutic agents for treating restless leg syndrome selected from a dopaminergic, such as Levodopa-carbidopa (Sinemet®, Sinemet CR®) or Levodopa-benzerazide (Prolopa®, Madopar®, Madopar HBS®); a sedative, such as clonazepam (Rivotril®); a dopamine agonists, such as bromocriptine (Parlodel®), pergolide (Permax®), pramipexole (Mirapex®), or ropinirole (Requip®); a narcotic agent, such as codeine (Tylenol #3®); or a GABAergic, such as gabapentin (Neurontin®).

In certain embodiments of the packages, preparations, compositions, and methods for the treatment of a movement disorder, the invention further comprises one or more therapeutic agents for treating tics selected from a sedative, such as clonazepam (Rivotril®); an alpha antagonist, such as clonidine (Catapress®); a dopamine reuptake inhibitor, such as tetrabenazine (Nitoman®); or a dopamine blocker, such as haloperidol (Haldol®) or perphenazine.

In certain embodiments of the packages, preparations, compositions, and methods for the treatment of a movement disorder, the invention further comprises one or more cyclooxygenase-2-selective inhibitors.

C. Pharmaceutical Preparations of DAT Inhibitors

In another aspect, the present invention provides pharmaceutical preparations comprising the subject DAT inhibitors. The DAT inhibitors for use in the subject method may be conveniently formulated for administration with a biologically acceptable, non-pyrogenic, and/or sterile medium, such as water, buffered saline, polyol (for example, glycerol, propylene glycol, liquid polyethylene glycol, and the like) or suitable mixtures thereof. The optimum concentration of the active ingredient(s) in the chosen medium can be determined empirically according to procedures well known to behavioral scientists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the DAT inhibitors, its use in the pharmaceutical preparation of the invention is contemplated. Suitable vehicles and their formulation inclusive of other proteins are described, for example, in the book Remington's Pharmaceutical Sciences (Remington's Pharmaceutical Sciences. Mack Publishing Company, Easton, Pa., USA 1985). These vehicles include injectable "deposit formulations."

Pharmaceutical formulations of the present invention can also include veterinary compositions, e.g., pharmaceutical preparations of the DAT inhibitors suitable for veterinary uses, e.g., for the treatment of livestock or domestic animals, e.g., dogs.

Methods of introduction may also be provided by rechargeable or biodegradable devices. Various slow release polymeric devices have been developed and tested in vivo in recent years for the controlled delivery of drugs. A variety of biocompatible polymers (including hydrogels), including both biodegradable and non-degradable polymers, can be used to form an implant for the sustained release of an DAT inhibitor at a particular target site. In accordance with the practice of this invention, it has been found that a dosage form and a method can be provided that administers an DAT inhibitor in a program that substantially lessens or completely compensates for tolerance in a patient. Tolerance, as defined in Pharmacology in Medicine, by Brill, p. 227 (1965) McGraw-Hill, is characterized as a decrease in effect followed by administering a drug. When tolerance develops following a single dose or a few doses over a very short time, it is referred to as acute tolerance. When the drug is administered over a more protracted period of time to show a demonstrable degree of tolerance, it is referred to as chronic tolerance. The medical literature, as exemplified in The Pharmacological Bases of Therapeutics, by Goodman and Gilman, 8th Ed., p. 72 (1990) Pergamon Press, reported tolerance may be acquired to the effects of many drugs and this literature classifies tolerance as acute or chronic based on when it is acquired. That is, acute tolerance develops during a dosing phase of one dose or on one day, and chronic tolerance is acquired due to chronic administration, typically weeks, months, and years.

In certain embodiments, particularly where the selected DAT inhibitor is one which may produce tolerance, e.g., acute tolerance, in the patient, it may be desirable to formulate the compound for variable dosing, and preferably for use in a dose-escalation regimen. In preferred embodiments, the subject DAT inhibitors are formulated to deliver a sustained and increasing dose, e.g., over at least 4 hours, and more preferably, over at least 8 or even 16 hours.

In certain embodiments, representative dosage forms include hydrogel matrix containing a plurality of tiny pills. The hydrogel matrix comprises a hydrophilic polymer, such as a polysaccharide, agar, agarose, natural gum, alkali alginate including sodium alginate, carrageenan, fucoidan, furcellaran, laminaran, hypnea, gum arabic, gum ghatti, gum karaya, gum tragacanth, locust bean gum, pectin, amylopectin, gelatin, and a hydrophilic colloid. The hydrogel matrix comprises a plurality of tiny pills (such as 4 to 50), each tiny pill comprising an increasing dose population of from 100 ng ascending in dose, such as 0.5 mg, 1 mg, 1.2 mg, 1.4 mg, 1.6 mg, 1.8 mg, etc. The tiny pills comprise a release rate controlling wall of 0.0 mm to 10 mm thickness to provide for the timed ascending release of drug. Representative wall-forming materials include a triglyceryl ester selected from glyceryl tristearate, glyceryl monostearate, glyceryl dipalmitate, glyceryl laureate, glyceryl didecenoate, and glyceryl tridecenoate. Other wall forming materials comprise polyvinyl acetate phthalate, methylcellulose phthalate, and microporous vinyl olefins. Procedures for manufacturing tiny pills are disclosed in U.S. Pat. Nos. 4,434,153; 4,721,613; 4,853,229; 2,996,431; 3,139,383, and 4,752,470, which are incorporated by reference herein.

In certain embodiments, the drug releasing beads are characterized by a dissolution profile wherein 0 to 20% of the beads undergo dissolution and release the drug in 0 to 2 hours, 20 to 40% undergo dissolution and release the drug in 2 to 4 hours, 40 to 60% exhibit dissolution and release in 4 to 6 hours, 60 to 80% in 6 to 8 hours, and 80 to 100% in 8 to 10 hours. The drug releasing beads can include a central composition or core comprising a drug and pharmaceutically acceptable composition forming ingredients including a lubricant, antioxidant, and buffer. The beads comprise increasing doses of drug, for example, 1 mg, 2 mg, 5 mg, and so forth to a high dose, in certain preferred embodiments, of 15 to 100 mg. The beads are coated with a release rate controlling polymer that can be selected utilizing the dissolution profile disclosed above. The manufacture of the beads can be adapted from, for example, Liu et al. (1994) Inter. J. of Pharm., 112:105-116; Liu et al. (1994) Inter. J. of Pharm., 112:117-124; Pharm. Sci., by Remington, 14th Ed. pp. 1626-1628 (1970); Fincher et al. (1968) J. Pharm. Sci., 57:1825-1835; and U.S. Pat. No. 4,083,949.

Another exemplary dosage form provided by the invention comprises a concentration gradient of DAT inhibitor from 1 mg to 15-600 mg coated from the former low dose to the latter high dose on a polymer substrate. The polymer can be an erodible or a nonerodible polymer. The coated substrate is rolled about itself from the latter high dose at the center of the dosage form, to the former low dose at the exposed outer end of the substrate. The coated substrate is rolled from the high dose to the low dose to provide for the release of from low to high dose as the substrate unrolls or erodes. For example, 1 mg to 600 mg of amphetamine is coated onto an erodible polymer such as an polypeptide, collagen, gelatin, or polyvinyl alcohol, and the substrate rolled concentrically from the high dose rolled over and inward to adapt a center position, and then outward towards the low dose to form an outer position. In operation, the dosage form erodes dispensing an ascending dose of amphetamine that is released over time.

Another dosage form provided by the invention comprises a multiplicity of layers, wherein each layer is characterized by an increasing dose of drug. The phrase "multiplicity of layers" denotes 2 to 6 layers in contacting lamination. The multiplicity of layers are positioned consecutively, that is, one layer after another in order, with a first exposed layer, the sixth layer in contact with the fifth layer and its exposed surface coated with a drug impermeable polymer. The sixth layer is coated with a drug impermeable polymer to insure release of the DAT inhibitor from the first layer to the sixth layer. The first layer comprises, for example, 1 to 50 mg of drug and each successive layer comprises an additional 1 to 50 mg of drug. The biodegradable polymers undergo chemical decomposition to form soluble monomers or soluble polymer units. The biodegradation of polymers usually involves chemically or enzymatically catalyzed hydrolysis. Representative of biodegradable polymers acceptable for an increase drug loading in each layer of from 5 to 50 wt % over the first and successive layers wherein the first layer comprises 100 ng. Representative biodegradable polymers comprise biodegradable poly(amides), poly(amino acids), poly(esters), poly(lactic acid), poly(glycolic acid), poly(orthoesters), poly(anhydrides), biodegradable poly(dehydropyrans), and poly(dioxinones). The polymers are known to the art in Controlled Release of Drugs, by Rosoff, Ch. 2, pp. 53-95 (1989); and in U.S. Pat. Nos. 3,811,444; 3,962,414; 4,066,747; 4,070,347; 4,079,038; and 4,093,709.

In still other embodiments, the invention employs a dosage form comprising a polymer that releases a drug by diffusion, flux through pores, or by rupture of a polymer matrix. The drug delivery polymeric system comprises a concentration gradient, wherein the gradient is an ascent in concentration from a beginning or initial concentration to a final, or higher concentration. The dosage form comprises an exposed surface at the beginning dose and a distant nonexposed surface at the final dose. The nonexposed surface is coated with a pharmaceutically acceptable material impermeable to the passage of drug. The dosage form structure provides for a flux increase delivery of drug ascending from the beginning to the final delivered dose.

The dosage form matrix can be made by procedures known in the polymer art. In one manufacture, 3 to 5 or more casting compositions are independently prepared wherein each casting composition comprises an increasing dose of drug with each composition overlayered from a low to the high dose. This provides a series of layers that come together to provide a unit polymer matrix with a concentration gradient. In another manufacture, the higher dose is cast first followed by laminating with layers of decreasing dose to provide a polymer matrix with a drug concentration gradient. An example of providing a dosage form comprises blending a pharmaceutically acceptable carrier, like polyethylene glycol, with a known dose of an DAT inhibitor and adding it to a silastic medical grade elastomer with a cross-linking agent, like stannous octanoate, followed by casting in a mold. The step is repeated for each successive layer. The system is allowed to set, e.g., for 1 hour, to provide the dosage form. Representative polymers for manufacturing the dosage form comprise olefin and vinyl polymers, condensation polymers, carbohydrate polymers, and silicon polymers as represented by poly(ethylene), poly(propylene), poly(vinyl acetate), poly(methyl acrylate), poly(isobutyl methacrylate), poly(alginate), poly(amide), and poly(silicone). The polymers and manufacturing procedures are known in Polymers, by Coleman et al., Vol. 31, pp. 1187-1230 (1990); Drug Carrier Systems, by Roerdink et al., Vol. 9, pp. 57-109 (1989); Adv. Drug Delivery Rev., by Leong et al., Vol. 1, pp. 199-233 (1987); Handbook of Common Polymers, compiled by Roff et al., (1971) published by CRC Press; and U.S. Pat. No. 3,992,518.

In still other embodiments, the subject formulations can be a mixture of different prodrug forms of one or more different DAT inhibitors, each prodrug form having a different hydrolysis rate, and therefore activation rate, to provide an increasing serum concentration of the active DAT inhibitors.

In other embodiments, the subject formulations can be a mixture of different DAT inhibitors, each compound having a different rate of adsorption (such as across the gut or epithelia) and/or serum half-life.

The dose-escalation regimen of the present invention can be used to compensate for the loss of a therapeutic effect of an DAT inhibitor, if any, by providing a method of delivery that continually compensates for the development of acute tolerance, by considering the clinical effect (E) of a drug at time (t) as a function of the drug concentration (C) according to Equation 1:

$$\text{Effect} = f(t, C)$$

In addition, the rate of drug delivered (A), in mg per hour, is inversely proportional to the concentration times the clearance of the drug. As the effect varies with time and the functionality is expressed, then, according to this invention, (A) can be governed to ensure the therapeutic effect is maintained at a clinical value. If the effect from a drug is found clinically to decrease with time, this decline could be linear as expressed by Equation 2:

$$\text{Effect}(t) = \text{Effect}(\text{ini}) - k\text{effect} * t$$

wherein, Effect(ini) is the clinical effect observed initially at the start of drug administration and Effect(t) is the effect observed at time (t) hours, keffect is a proportionality constant ascertained by measuring the clinical effect (E1) at time (t1) hours and (E2) at time (t2) hours while maintaining a constant plasma concentration followed by dividing (E1) minus (E2) by (t1) minus (t2). In order to maintain a constant effect, (A) must be adjusted with the same functionality according to Equation 3:

$$A(t) = A(\text{ini}) + k\text{effect} * t$$

wherein A(ini) is the initial drug input in mg per hour at the start of the therapy and A(t) is the drug input at time (t) hours, and keffect is the proportionality constant presented above. If the therapeutic effect is found to decline exponentially with time, this relationship is expressed by Equation 4:

$$\text{Effect}(t) = \text{Effect}(\text{ini}) * \exp(-k\text{effect} * t)$$

wherein Effect(ini) and Effect(t) are as defined before, keffect is a rate constant ($h^{-1}$), a unit of reciprocal hours, ascertained by measuring the clinical effect (E1) at time (t1) hours and (E2) at time (t2) hours while maintaining a constant plasma concentration followed by dividing natural log of (E1) minus natural log of (E2) by (t1) minus (t2). To maintain a constant effect, (A) must be adjusted according to Equation 5:

$$A(t) = A(\text{ini}) * \exp(k\text{effect} * t)$$

wherein A(ini) and A(t) are as defined before, keffect is the rate constant ($h^{-1}$) presented above. The equations are presented in Holford et al. (1982) Pharmac. Ther., 16:143-166.

The preparations of the present invention may be given orally, parenterally, topically, or rectally. They are of course given by forms suitable for each administration route. For example, they are administered in tablets or capsule form, by injection, infusion, inhalation, rectal suppository, or controlled release patch. Oral and controlled release patch administrations are preferred.

In certain preferred embodiments, the subject therapeutic is delivered by way of a transdermal patch. A patch is generally a flat hollow device with a permeable membrane on one side and also some form of adhesive to maintain the patch in place on the patient's skin, with the membrane in contact with the skin so that the medication can permeate out of the patch reservoir and into and through the skin. The outer side of the patch is formed of an impermeable layer of material, and the membrane side and the outer side are joined around the perimeter of the patch, forming a reservoir for the medication and carrier between the two layers.

Patch technology is based on the ability to hold an active ingredient in constant contact with the epidermis. Over substantial periods of time, drug molecules, held in such a state, will eventually find their way into the bloodstream. Thus, patch technology relies on the ability of the human body to pick up drug molecules through the skin. Transdermal drug delivery using patch technology has recently been applied for delivery of nicotine in an effort to assist smokers in quitting, the delivery of nitroglycerine to angina sufferers, the delivery of replacement hormones in post menopausal women, etc. These conventional drug delivery systems comprise a patch with an active ingredient such as a drug incorporated therein, the patch also including an adhesive for attachment to the skin so as to place the active ingredient in close proximity to the skin. Exemplary patch technologies are available from Ciba-Geigy Corporation and Alza Corporation. Such transdermal delivery devices can be readily adapted for use with the subject DAT inhibitors.

The flux of the subject DAT inhibitors across the skin can be modulated by changing either (a) the resistance (the diffusion coefficient), or (b) the driving force (the solubility of the drug in the stratum corneum and consequently the gradient for diffusion). Various methods can be used to increase skin permeation by the subject DAT inhibitors, including penetration enhancers, use of pro-drug versions, superfluous vehicles, iontophoresis, phonophoresis, and thermophoresis. Many enhancer compositions have been developed to change one or both of these factors. See, for example, U.S. Pat. Nos. 4,006,218; 3,551,154; and 3,472,931, which respectively describe the use of dimethylsulfoxide (DMSO), dimethyl formamide (DMF), and N,N-dimethylacetamide (DMA) for enhancing the absorption of topically applied drugs through the stratum corneum. Combinations of enhancers consisting of diethylene glycol monoethyl or monomethyl ether with propylene glycol monolaurate and methyl laurate are disclosed in U.S. Pat. No. 4,973,468. A dual enhancer consisting of glycerol monolaurate and ethanol for the transdermal delivery of drugs is shown in U.S. Pat. No. 4,820,720. U.S. Pat. No. 5,006,342 lists numerous enhancers for transdermal drug administration consisting of fatty acid esters or fatty alcohol ethers of C2 to C4 alkanediols, where each fatty acid/alcohol portion of the ester/ether is of about 8 to 22 carbon atoms. U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a C2 or C3 alkanol; and an inert diluent such as water. Other examples are included in the teachings of U.S. Pat. No. 4,933,184 which discloses the use of menthol as a penetration enhancer; U.S. Pat. No. 5,229,130 which discloses the use of vegetable oil (soybean and/or coconut oil) as a penetration enhancer; and U.S. Pat. No. 4,440,777 which discloses the use of eucalyptol as a penetration enhancer.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration," and "administered peripherally" as used herein mean the administration of a compound, drug, or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular DAT inhibitors employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular, and subcutaneous doses of the compounds of this invention for a patient will range from about 0.0001 to about 100 mg per kilogram of body weight per day.

If desired, the effective daily dose of the active compound may be administered as two, three, four, five, six, or more sub-doses administered separately at appropriate intervals throughout the day, optionally, in unit dosage forms.

The term "treatment" is intended to encompass also prophylaxis, therapy, and cure.

The patient receiving this treatment is any animal in need, including primates, in particular, humans and other mammals such as equines, cattle, swine, and sheep; and poultry and pets in general.

The compound of the invention can be administered as such or in admixtures with pharmaceutically acceptable carriers and can also be administered in conjunction with other drugs such as dopamine precursors, dopaminergic agents, dopaminergic and anti-cholinergic agents, anti-cholinergic agents, dopamine agonists, MAO-B (monoamine oxidase B) inhibitors, COMT (catechol O-methyltransferase) inhibitors, muscle relaxants, sedatives, anticonvulsant agents, dopamine reuptake inhibitors, dopamine blockers, β-blockers, carbonic anhydrase inhibitors, narcotic agents, GABAergic agents, or alpha antagonists. Conjunctive therapy thus includes sequential, simultaneous and separate administration of the active compound in a way that the therapeutic effects of the first one administered are not entirely absent when the subsequent is administered.

While it is possible for a compound of the present invention to be administered alone, it is preferable to administer the compound as a pharmaceutical formulation (composition). The DAT inhibitors according to the invention may be formulated for administration in any convenient way for use in human or veterinary medicine.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, or pastes for application to the tongue; (2) parenteral administration, for example, by subcutaneous, intramuscular, or intravenous injection as, for example, a sterile solution or suspension; (3) topical application, for example, as a cream, ointment, or spray applied to the skin; or (4) intravaginally or intrarectally, for example, as a pessary, cream, or foam. However, in certain embodiments, the subject compounds may be simply dissolved or suspended in sterile water.

The phrase "pharmaceutically acceptable carrier" as used herein means a pharmaceutically acceptable material, composition, or vehicle, such as a liquid or solid filter, diluent, excipient, solvent, or encapsulating material, involved in carrying or transporting the subject regulators from one organ or portion of the body to another organ or portion of the body. Each carrier must be "acceptable" in the sense of being compatible with the other ingredients of the formulation and not injurious to the patient. Some examples of materials which can serve as pharmaceutically acceptable carriers include (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present DAT inhibitors may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid and isolating the salt thus formed. Representative salts include but are not limited to following: 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cyclopentanepropionate, digluconate, dodecylsulfate, edetate, edisylate, estolate, esylate, ethanesulfonate, fumarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, isothionate, lactate, lactobionate, laurate, laurylsulphonate, malate, maleate, mandelate, mesylate, methanesulfonate, methylbromide, methylnitrate, methylsulfate, mucate, naphthylate, napsylate, nicotinate, nitrate, N-methylglucamine ammonium salt, oleate, oxalate, palmitate, pamoate, pantothenate, pectinate, persulfate, phosphate, phosphate/diphosphate, picrate, pivalate, polygalacturonate, propionate, p-toluenesulfonate, salicylate, stearate, subacetate, succinate, sulfate, sulfosaliculate, suramate, tannate, tartrate, teoclate, thiocyanate, tosylate, triethiodide, undecanoate, and valerate salts, and the like. (See, for example, Berge et al. (1977) "Pharmaceutical Salts," J. Pharm. Sci. 66:1-19).

In certain embodiments, the pharmaceutically acceptable salts of the subject compounds include the conventional non-toxic salts of the compounds, e.g., from non-toxic organic or inorganic acids. Particularly suitable are salts of weak acids. For example, such conventional non-toxic salts include those derived from inorganic acids such as hydrochloric, hydrobromic, hydriodic, cinnamic, gluconic, sulfuric, sulfamic, phosphoric, nitric, and the like; and the salts prepared from organic acids such as acetic, propionic, succinic, glycolic, stearic, lactic, maleic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like. (See, for example, Berge et al., supra).

Wetting agents, emulsifiers, and lubricants, such as sodium lauryl sulfate and magnesium stearate, as well as coloring agents, release agents, coating agents, sweetening, flavoring and perfuming agents, preservatives, and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal, and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), and/or as mouth washes, and the like, each containing a predetermined amount of a compound of the present invention as an active ingredient. A compound of the present invention may also be administered as a bolus, electuary, or paste.

In solid dosage forms of the invention for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), or surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents, and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, and sweetening, flavoring, coloring, perfuming, and preservative agents.

Suspensions, in addition to the active compounds, may contain suspending agents, such as ethoxylated isostearyl alcohols, polyoxyethylene sorbitol and sorbitan esters, microcrystalline cellulose, aluminum metahydroxide, bentonite, agar-agar, and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax, or a salicylate, and which is solid at room temperature, but liquid at body temperature and, therefore, will melt in the rectum or vaginal cavity and release the active DAT inhibitor.

Formulations of the present invention which are suitable for vaginal administration also include pessaries, tampons, creams, gels, pastes, foams, or spray formulations containing such carriers as are known in the art to be appropriate.

Dosage forms for the topical or transdermal administration of a compound of this invention include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required.

The ointments, pastes, creams, and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound of this invention, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, the subject compound(s) are formulated as part of a transdermal patch. Transdermal patches have the added advantage of providing controlled delivery of a compound of the present invention to the body. Such dosage forms can be made by dissolving or dispersing the DAT inhibitors in the proper medium. Absorption enhancers can also be used to increase the flux of the DAT inhibitors across the skin. The rate of such flux can be controlled by either providing a rate-controlling membrane or dispersing the compound in a polymer matrix or gel.

The "free base form" of the subject compound relates to a form in which the compound is not complexed with an acid, e.g., is not an ammonium salt. Such forms may be incorporated into a patch. It will be appreciated that the DAT inhibitors may be complexed, for example, with elements of the drug-retaining matrix of the patch and, as such, the DAT inhibitors may not necessarily be in the form of the free base, when actually retained by the patch.

The patch preferably comprises a drug-impermeable backing layer. Suitable examples of drug-impermeable backing layers which may be used for transdermal or medicated patches include films or sheets of polyolefins, polyesters, polyurethanes, polyvinyl alcohols, polyvinyl chlorides, polyvinylidene chloride, polyamides, ethylene-vinyl acetate copolymer (EVA), ethylene-ethylacrylate copolymer (EEA), vinyl acetate-vinyl chloride copolymer, cellulose acetate, ethyl cellulose, metal vapour deposited films or sheets thereof, rubber sheets or films, expanded synthetic resin sheets or films, non-woven fabrics, fabrics, knitted fabrics, paper, and foils. Preferred drug-impermeable, elastic backing materials are selected from polyethylene terephthalate (PET), polyurethane, ethylene-vinyl acetate copolymer (EVA), plasticized polyvinylchloride, and woven and non-woven fabric. Especially preferred is non-woven polyethylene terephthalate (PET). Other backings will be readily apparent to those skilled in the art.

The term "block copolymer," in the preferred adhesives of the invention, refers to a macromolecule comprised of two or more chemically dissimilar polymer structures, terminally connected together (Block Copolymers: Overview and Critical Survey, Noshay and McGrath, 1977). These dissimilar polymer structures, sections or segments, represent the "blocks" of the block copolymer. The blocks may generally be arranged in an A-B structure, an A-B-A structure, or a multi-block -(A-B)n-system, wherein A and B are the chemically distinct polymer segments of the block copolymer.

It is generally preferred that the block copolymer is of an A-B-A structure, especially wherein one of A and B is an acrylic-type polymeric unit. It will be appreciated that the present invention is also applicable using block copolymers which possess three or more different blocks, such as an A-B-C block copolymer. However, for convenience, reference hereinafter to block copolymers will assume that there are only A and B sub-units, but it will be appreciated that such reference also encompasses block copolymers having more than two different sub-units, unless otherwise specified.

It will be appreciated that the properties of block copolymers are very largely determined by the nature of the A and B blocks. Block copolymers commonly possess both 'hard' and 'soft' segments. A 'hard' segment is a polymer that has a glass transition temperature (Tg) and/or a melting temperature (Tm) that is above room temperature, while a 'soft' segment is a polymer that has a Tg (and possibly a Tm) below room temperature. The different segments are thought to impart different properties to the block copolymer. Without being constrained by theory, it is thought that association of the hard segments of separate block copolymer units result in physical cross-links within the block copolymer, thereby promoting cohesive properties of the block copolymer. It is particularly preferred that the hard segments of the block copolymers form such physical close associations.

The block copolymers useful in the present invention preferably are acrylic block copolymers. In acrylic block copolymers, at least one of the blocks of the block copolymer is an acrylic acid polymer or a polymer of an acrylic acid derivative. The polymer may be composed of just one repeated monomer species. However, it will be appreciated that a mixture of monomeric species may be used to form each of the blocks, so that a block may, in itself, be a copolymer. The use of a combination of different monomers can affect various properties of the resulting block copolymer. In particular, variation in the ratio or nature of the monomers used allows properties such as adhesion, tack, and cohesion to be modulated, so that it is generally advantageous for the soft segments of the block copolymer to be composed of more than one monomer species.

It is preferred that alkyl acrylates and alkyl methacrylates are polymerized to form the soft portion of the block copolymer. Alkyl acrylates and alkyl methacrylates are thought to provide properties of tack and adhesion. Suitable alkyl acrylates and alkyl methacrylates include n-butyl acrylate, n-butyl methacrylate, hexyl acrylate, 2-ethylbutyl acrylate, isooctyl acrylate, 2-ethylhexyl acrylate, 2-ethylhexyl methacrylate, decyl acrylate, decyl methacrylate, dodecyl acrylate, dodecyl methacrylate, tridecylacrylate, and tridecyl methacrylate, although other suitable acrylates and methacrylates will be readily apparent to those skilled in the art. It is preferred that the acrylic block copolymer comprises at least 50% by weight of alkyl acrylate or alkyl methacrylate(co)polymer.

Variation in the components of the soft segment affects the overall properties of the block copolymer, although the essential feature remains the cross-linking of the soft segments. For example, soft segments essentially consisting of diacetone acrylamide with either butyl acrylate and/or 2-ethylhexyl acrylate, in approximately equal proportions, work well, and a ratio by weight of about 3:4:4 provides good results. It is preferred that diacetone acrylamide or other polar monomer, such as hydroxyethylmethacrylate or vinyl acetate, be present in no more than 50% w/w of the monomeric mix of the soft segment, as this can lead to reduced adhesion, for example. The acrylate component may generally be varied more freely, with good results observed with both 2-ethylhexyl acrylate and butyl acrylate together or individually.

As noted above, ratios of the various monomers are generally preferred to be approximately equal. For adhesives, this is preferred to be with a polar component of 50% or less of the soft segment, with the apolar portion forming up to about 85% w/w, but preferably between about 50 and 70% w/w. In the example above, this is about 72% (4+4) polar to about 18% (3) polar.

In general, it is particularly preferred that any apolar monomer used does not confer acidity on the adhesive. Adhesives of the invention are preferably essentially neutral, avoiding any unnecessary degeneration of the DAT inhibitors.

Limiting active functionalities, especially those with active hydrogen, is generally preferred, in order to permit wide use of any given formulation of adhesive without having to take into account how it is likely to interact chemically with its environment. Thus, a generally chemically inert adhesive is preferred, in the absence of requirements to the contrary.

As discussed above, polymers suitable for use as the hard portion of the block copolymer possess glass transition temperatures above room temperature. Suitable monomers for use in forming the hard segment polymer include styrene, x-methylstyrene, methyl methacrylate, and vinyl pyrrolidone, although other suitable monomers will be readily apparent to those skilled in the art. Styrene and polymethylmethacrylate have been found to be suitable for use in the formation of the hard segment of the block copolymers. It is preferred that the hard portion of the block copolymer forms from 3-30% w/w of the total block copolymer, particularly preferably from 5-15% w/w.

The block copolymer is further characterized in that the soft portions contain a degree of chemical cross-linking. Such cross-linking may be effected by any suitable cross-linking agent. It is particularly preferable that the cross-linking agent be in the form of a monomer suitable for incorporation into the soft segment during polymerization. Preferably the cross-linking agent has two or more radically polymerizable groups, such as a vinyl group, per molecule of the monomer, at least one tending to remain unchanged during the initial polymerization, thereby permitting cross-linking of the resulting block copolymer.

Suitable cross-linking agents for use in the present invention include divinylbenzene, methylene bis-acrylamide, ethylene glycol di(meth)acrylate, ethyleneglycol tetra(meth)acrylate, propylene glycol di(meth)acrylate, butylene glycoldi(meth)acrylate, or trimethylolpropane tri(meth)acrylate, although other suitable cross-linking agents will be readily apparent to those skilled in the art. A preferred cross-linking agent is tetraethylene glycol dimethacrylate. It is preferred that the cross-linking agent comprises about 0.01-0.6% by weight of the block copolymer, with 0.1-0.4% by weight being particularly preferred.

Methods for the production of block copolymers from their monomeric constituents are well known. The block copolymer portions of the present invention may be produced by any suitable method, such as step growth, anionic, cationic, and free radical methods (Block Copolymers, supra). Free radical methods are generally preferred over other methods, such as anionic polymerization, as the solvent and the monomer do not have to be purified.

Suitable initiators for polymerization include polymeric peroxides with more than one peroxide moiety per molecule. An appropriate choice of reaction conditions is well within the skill of one in the art, once a suitable initiator has been chosen.

The initiator is preferably used in an amount of 0.005-0.1% by weight of the block copolymer, with 0.01-0.05% by weight being particularly preferred, although it will be appreciated that the amount chosen is well within the skill of one in the art. In particular, it is preferred that the amount should not be so much as to cause instant gelling of the mix, nor so low as to slow down polymerization and to leave excess residual monomers. A preferred level of residual monomers is below 2000 ppm.

It will also be appreciated that the amount of initiator will vary substantially, depending on such considerations as the initiator itself and the nature of the monomers.

The block copolymers are adhesives, and preferably are pressure sensitive adhesives. Pressure sensitive adhesives can be applied to a surface by hand pressure and require no activation by heat, water, or solvent. As such, they are particularly suitable for use in accordance with the present invention.

The block copolymers may be used without tackifiers and, as such, are particularly advantageous. However, it will be appreciated that the block copolymers may also be used in combination with a tackifier, to provide improved tack, should one be required or desired. Suitable tackifiers are well known and will be readily apparent to those skilled in the art.

Without being constrained by theory, it is thought that the combination of chemical cross-links between the soft segments of the copolymer combined with the, generally, hydrophobic interaction, or physical cross-linking, between the hard portions results in a "matrix-like" structure. Copolymers having only physical cross-linking of the hard segments are less able to form such a matrix. It is believed that the combination of both forms of cross-linking of the block copolymers provides good internal strength (cohesion) and also high drug storage capacity.

More particularly, it is believed that the hard segments associate to form "islands," or nodes, with the soft segments radiating from and between these nodes.

There is a defined physical structure in the "sea" between the islands, where the soft segments are cross-linked, so that there is no necessity for extensive intermingling of the soft segments. This results in a greater cohesion of the whole block copolymer while, at the same time, allowing shortened soft segment length and still having as great, or greater, distances between the islands, thereby permitting good drug storage capacity.

The block copolymer preferably cross-links as the solvent is removed, so that cross-linking can be timed to occur after coating, this being the preferred method.

Accordingly, not only can the block copolymer easily be coated onto a surface, but the complete solution can also be stored for a period before coating. Accordingly, in the manufacturing process of the patches, the process preferably comprises polymerizing the monomeric constituents of each soft segment in solution, then adding the constituents of the hard segment to each resulting solution and polymerizing the resulting mix, followed by cross-linking by removal of any solvent or solvent system, such as by evaporation. If the solution is to be stored for any length of time, it may be necessary to keep the polymer from precipitating out which may be achieved by known means, such as by suspending agents or shaking. It may also be necessary to select the type of polymers that will be subject to substantially no cross-linking until the solvent is evaporated.

In general, it is preferred that the adhesive possesses a minimum number of functionalities having active hydrogen, in order to avoid undesirable reactions/interactions, such as with any drug that it is desired to incorporate into the adhesive material. It will be appreciated that this is only a preferred restriction, and that any adhesive may be tailored by one skilled in the art to suit individual requirements.

Suitable monomers for use in forming the hard segment include styrene, a-methylstyrene, methyl methacrylate, and vinyl pyrrolidone, with the preferred proportion of the hard segment being between 5 and 15% w/w. In particular, it is advantageous to use the compounds of WO 99/02141, as it is possible to load over 30% of drug into such a system.

Thus, in the patches of the present invention, it is generally possible to calculate the amount of drug required and determine the appropriate patch size with a given drug loading in accordance with a patient's body weight which can be readily calculated by those skilled in the art.

In certain embodiments, small amounts of plasticizer, such as isopropyl myristate (IPM), are incorporated. This has the advantage of helping solubilize the DAT inhibitor(s) as well as rendering the adhesive less rough on the skin. Levels of between 2 and 25%, by weight, are generally useful, with levels of between 3 and 20% being more preferred and levels of 5 to 15%, especially about 10%, being most preferred. Other plasticizers may also be used, and suitable plasticizers will be readily apparent to those skilled in the art.

Plasticizers generally take the form of oily substances introduced into the adhesive polymer. The effect of the introduction of such oily substances is to soften the physical structure of the adhesive whilst, at the same time, acting at the interface between the adhesive and the skin, thereby helping to somewhat weaken the adhesive, and to reduce exfoliation.

The free base oil may be obtained by basifying salts of the subject compounds, or any other suitable salt, with a suitable base, in the presence of a hydrophilic solvent, especially water, and an organic solvent. For instance, water and ethyl acetate, in approximately equal proportions, work well, with ammonia serving as the basifying agent. The water may then be removed and the preparation washed with further water, or other aqueous preparation, after which the preparation may be suitably extracted with ether, for example, after having removed the ethyl acetate. It is preferred to keep the preparation under an inert atmosphere, especially after completion.

Whilst it will be appreciated that patches of the present invention may be removed from the patient at any time once it is desired to terminate a given dose, this can have the disadvantage of providing an opportunity for potential drug abuse of the partially discharged patch. Abuse of the subject compounds is highly undesirable.

In certain embodiments, it may be advantage to use a patch tailored to have delivered, by about 8 hours after application, the majority of the subject compound that it is capable of delivering in a 24 hour period, so that a patch can be left in place, and levels of drug still diminish appreciably. It is advantageous that the drug delivery profile has first order kinetics, so that the majority of the drug is delivered during the main part of the day and, even if the patient omits to remove the patch, the amount of drug is moving towards exhaustion by the end of the day, and the amount of drug is dropping rapidly.

It will be appreciated that patches of the invention may be constructed in any suitable manner known in the art for the manufacture of transdermal patches. The patches may simply comprise adhesive, drug, and backing, or may be more complex, such as having edging to prevent seepage of drug out of the sides of the patch. Patches may also be multi-layered.

Ophthalmic formulations, eye ointments, powders, solutions, and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient, or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition," W.H. Freedman and Co., San Francisco, U.S.A., 1969 or "Livestock Feeds and Feeding" O and B books, Corvallis, Ore., U.S.A., 1977).

IV. Biochemical Activity at Cellular Receptors, and Assays to Detect that Activity Assaying processes are well known in the art in which a reagent is added to a sample, and measurements of the sample and reagent are made to identify sample attributes stimulated by the reagent. For example, one such assay process concerns determining in a chromogenic assay the amount of an enzyme present in a biological sample or solution. Such assays are based on the development of a colored product in the reaction solution. The reaction develops as the enzyme catalyzes the conversion of a colorless chromogenic substrate to a colored product.

Another assay useful in the present invention concerns determining the ability of a ligand to bind to a biological receptor utilizing a technique well known in the art referred to as a radioligand binding assay. This assay accurately determines the specific binding of a radio-ligand to a targeted receptor through the delineation of its total and nonspecific binding components. Total binding is defined as the amount of radio-ligand that remains following the rapid separation of the radio-ligand bound in a receptor preparation (cell homogenates or recombinate receptors) from that which is unbound. The nonspecific binding component is defined as the amount of radio-ligand that remains following separation of the reaction mixture consisting of receptor, radio-ligand and an excess of unlabeled ligand. Under this condition, the only radio-ligand that remains represents that which is bound to components other that receptor. The specific radio-ligand bound is determined by subtracting the nonspecific from total radioactivity bound. For a specific example of radio-ligand binding assay for μ-opioid receptor, see Wang, J. B. et al. FEBS Letters 1994, 338, 217.

Assays useful in the present invention concern determining the activity of receptors the activation of which initiates subsequent intracellular events in which intracellular stores of calcium ions are released for use as a second messenger. Activation of some O-protein-coupled receptors stimulates the formation of inositol triphosphate (IP3, a O-protein-coupled receptor second messenger) through phospholipase C-mediated hydrolysis of phosphatidylinositol, Berridge and Irvine (1984). Nature 312:315-21. IP3 in turn stimulates the release of intracellular calcium ion stores.

A change in cytoplasmic calcium ion levels caused by release of calcium ions from intracellular stores is used to determine G-protein-coupled receptor function. This is another type of indirect assay. Among G-protein-coupled receptors are muscarinic acetylcholine receptors (mAChK), adrenergic receptors, sigma receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such, as EGTA, to distinguish fluorescence response resulting from calcium release from internal stores. Another type of indirect assay involves determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGNIP levels of the cytoplasm.

Furthermore, there are cyclic nucleotide-gated ion channels, e.g., rod photoreceptor cell channels and olfactory neuron channels [see, Altenhofen, W. et al. (1991) Proc. Natl. Acad. Sci 88:9868-9872 and Dhallan et al. (1990) Nature 347:184-187] that are permeable to cations upon activation by binding of cAMP or cGMP. A change in cytoplasmic ion levels caused by a change in the amount of cyclic nucleotide activation of photo-receptor or olfactory neuron channels is used to determine function of receptors that cause a change in CAMP or cGMP levels when activated. In cases where activation of the receptor results in a decrease in cyclic nucleotide levels, it may be preferable to expose the cells to agents that increase intracellular cyclic nucleotide levels, e.g., forskolin, prior to adding a receptactivating compound to the cells in the assay. Cell for this type of assay can be made by co-transfection of a host cell with DNA encoding a cyclic nucleotide-gated ion channel and a DNA encoding a receptor (e.g., certain metabotropic glutamate receptors, muscarinic acetylcholine receptors, dopamine receptors, serotonin receptors and the like, which, when activated, causes a change in cyclic nucleotide levels in the cytoplasm.

Any cell expressing a receptor protein which is capable, upon activation, of directly increasing the intracellular concentration of calcium, such as by opening gated calcium channels, or indirectly affecting the concentration of intracellular calcium as by causing initiation of a reaction which utilizes $Ca^{2+}$ as a second messenger (e.g., G-protein-coupled receptors), may form the basis of an assay. Cells endogenously expressing such receptors or ion channels, and cells which may be transfected with a suitable vector encoding one or more such cell surface proteins are known to those of skill in the art, or may be identified by those of skill in the art. Although essentially any cell which expresses endogenous ion channel and/or receptor activity may be used, it is preferred to use cells transformed or transfected with heterologous DNAs encoding such ion channels and/or receptors so as to express predominantly a single type of ion channel or receptor. Many cells that may be genetically engineered to express a heterologous cell surface protein are known. Such cells include, but are not limited to, baby hamster kidney (BHK) cells (ATCC No. CCL10), mouse L cells (ATCC No. CCLI.3), DG44 cells [see, Chasin (1986) Cell. Moles. Genet. 12:555] human embryonic kidney (HEK) cells (ATCC No. CRL1573), Chinese hamster ovary (CHO) cells (ATCC Nos. CRL9618, CCL61, CRL9096), PC12 cells (ATCC No. CRL1721) and COS-7 cells (ATCC No. CRL1651). Preferred cells for heterologous cell surface protein expression are those that can be readily and efficiently transfected. Preferred cells include HEK 293 cells, such as those described in U.S. Pat. No. 5,024,939.

Any compound which is known to activate ion channels or receptors of interest may be used to initiate an assay. Choosing an appropriate ion channel- or receptactivating reagent depending on the ion channel or receptor of interest is within the skill of the art. Direct depolarization of the cell membrane to determine calcium channel activity may be accomplished by adding a potassium salt solution having a concentration of potassium ions such that the final concentration of potassium ions in the cell-containing well is in the range of about 50-150 mM (e.g., 50 mM KCl). With respect to ligand-gated receptors and ligand-gated ion channels, ligands are known which have affinity for and activate such receptors. For example, nicotinic acetyloholine receptors are known to be activated by nicotine or acetylcholine; similarly, muscarinic and acetylcholine receptors may be activated by addition of muscarine or carbamylcholine.

Agonist assays may be carried out on cells known to possess ion channels and/or receptors to determine what effect, if any, a compound has on activation or potentiation of ion channels or receptors of interest. Agonist assays also may be carried out using a reagent known to possess ion channel- or receptactivating capacity to determine whether a cell expresses the respective functional ion channel or receptor of interest.

Contacting a functional receptor or ion channel with agonist typically activates a transient reaction; and prolonged exposure to an agonist may desensitize the receptor or ion channel to subsequent activation. Thus, in general, assays for determining ion channel or receptor function should be initiated by addition of agonist (i.e., in a reagent solution used to initiate the reaction). The potency of a compound having agonist activity is determined by the detected change in some observable in the cells (typically an increase, although activation of certain receptors causes a decrease) as compared to the level of the observable in either the same cell, or substantially identical cell, which is treated substantially identically except that reagent lacking the agonist (i.e., control) is added to the well. Where an agonist assay is performed to test whether or not a cell expresses the functional receptor or ion channel of interest, known agonist is added to test-cell-containing wells and to wells containing control cells (substantially identical cell that lacks the specific receptors or ion channels) and the levels of observable are compared. Depending on the assay, cells lacking the ion channel and/or receptor of interest should exhibit substantially no increase in observable in response to the known agonist. A substantially identical cell may be derived from the same cells from which recombinant cells are prepared but which have not been modified by introduction of heterologous DNA. Alternatively, it may be a cell in which the specific receptors or ion channels are removed. Any statistically or otherwise significant difference in the level of observable indicates that the test compound has in some manner altered the activity of the specific receptor or ion channel or that the test cell possesses the specific functional receptor or ion channel.

In an example of drug screening assays for identifying compounds which have the ability to modulate ion channels or receptors of interest, individual wells (or duplicate wells, etc.) contain a distinct cell type, or distinct recombinant cell line expressing a homogeneous population of a receptor or ion channel of interest, so that the compound having unidentified activity may be screened to determine whether it possesses modulatory activity with respect to one or more of a variety of functional ion channels or receptors. It is also contemplated that each of the individual wells, may contain the same cell type so that multiple compounds (obtained from different reagent sources in the apparatus or contained within different wells) can be screened and compared for modulating activity with respect to one particular receptor or ion channel type.

Antagonist assays, including drug screening assays, may be carried out by incubating cells having functional ion channels and/or receptors in the presence and absence of one or more compounds, added to the solution bathing the cells in the respective wells of the microtiter plate for an amount of time sufficient (to the extent that the compound has affinity for the ion channel and/or receptor of interest) for the compound(s) to bind to the receptors and/or ion channels, then activating the ion channels or receptors by addition of known agonist, and measuring the level of observable in the cells as compared to the level of observable in either the same cell, or substantially identical cell, in the absence of the putative antagonist.

The assays are thus useful for rapidly screening compounds to identify those that modulate any receptor or ion channel in a cell. In particular, assays can be used to test functional ligand-receptor or ligand-ion channel interactions for cell receptors including ligand-gated ion channels, voltage-gated ion channels, G-protein-coupled receptors and growth factor receptors.

Those of ordinary skill in the art will recognize that assays may encompass measuring a detectable change of a solution as a consequence of a cellular event which allows a compound, capable of differential characteristics, to change its characteristics in response to the cellular event. By selecting a particular compound which is capable of differential characteristics upon the occurrence of a cellular event, various assays may be performed. For example, assays for determining the capacity of a compound to induce cell injury or cell death may be carried out by loading the cells with a pH-sensitive fluorescent indicator such as BCECF (Molecular Probes, Inc., Eugene, Oreg. 97402, Catalog #B1150) and measuring cell-injury or -cell-death as a function of changing fluorescence over time.

In a further example of useful assays, the function of receptors whose activation results in a change in the cyclic nucleotide levels of the cytoplasm may be directly determined in assays of cells that express such receptors and that have been injected with a fluorescent compound that changes fluorescence upon binding cAMP. The fluorescent compound comprises cAMPdependent-protein kinase in which the catalytic and regulatory subunits are each labelled with a different fluorescent-dye [Adams et al. (1991) Nature 349:694-697]. When cAMP binds to the regulatory subunits, the fluorescence emission spectrum changes; this change can be used as an indication of a change in cAMP concentration.

The function of certain neurotransmitter transporters which are present at the synaptic cleft at the junction between two neurons may be determined by the development of fluorescence in the cytoplasm of such neurons when conjugates of an amine acid and fluorescent indicator (wherein the fluorescent indicator of the conjugate is an acetoxymethyl ester derivative e.g., 5-(aminoacetamido)fluorescein; Molecular Probes, Catalog #A1363) are transported by the neurotransmitter transporter into the cytoplasm of the cell where the ester group is cleaved by esterase activity and the conjugate becomes fluorescent.

In practicing an assay of this type, a reporter gene construct is inserted into an eukaryotic cell to produce a recombinant cell which has present on its surface a cell surface protein of a specific type. The cell surface receptor may be endogenously expressed or it may be expressed from a heterologous gene that has been introduced into the cell. Methods for introducing heterologous DNA into eukaryotic cells are-well known in the art and any such method may be used. In addition, DNA encoding various cell surface proteins is known to those of skill in the art or it may be cloned by any method known to those of skill in the art.

The recombinant cell is contacted with a test compound and the level of reporter gene expression is measured. The contacting may be effected in any vehicle and the testing may be by any means using any protocols, such as serial dilution, for assessing specific molecular interactions known to those of skill in the art. After contacting the recombinant cell for a sufficient time to effect any interactions, the level of gene expression is measured. The amount of time to effect such interactions may be empirically determined, such as by running a time course and measuring the level of transcription as a function of time. The amount of transcription may be measured using any method known to those of skill in the art to be suitable. For example, specific mRNA expression may be detected using Northern blots or specific protein product may be identified by a characteristic stain. The amount of transcription is then compared to the amount of transcription in either the same cell in the absence of the test compound or it may be compared with the amount of transcription in a substantially identical cell that lacks the specific receptors. A substantially identical cell may be derived from the same cells from which the recombinant cell was prepared but which had not been modified by introduction of heterologous DNA. Alternatively, it may be a cell in which the specific receptors are removed. Any statistically or otherwise significant difference in the amount of transcription indicates that the test compound has in some manner altered the activity of the specific receptor.

If the test compound does not appear to enhance, activate or induce the activity of the cell surface protein, the assay may be repeated and modified by the introduction of a step in which the recombinant cell is first tested for the ability of a known agonist or activator of the specific receptor to activate transcription if the transcription is induced, the test compound is then assayed for its ability to inhibit, block or otherwise affect the activity of the agonist.

The transcription based assay is useful for identifying compounds that interact with any cell surface protein whose activity ultimately alters gene expression. In particular, the assays can be used to test functional ligand-receptor or ligand-ion channel interactions for a number of categories of cell surface-localized receptors, including: ligand-gated ion channels and voltage-gated ion channels, and protein-coupled receptors.

Any transfectable cell that can express the desired cell surface protein in a manner such the protein functions to intracellularly transduce an extracellular signal may be used. The cells may be selected such that they endogenously express the cell surface protein or may be genetically engineered to do so. Many such cells are known to those of skill in the art. Such cells include, but are not limited to Ltk⁻ cells, PC12 cells and COS-7 cells.

Any cell surface protein that is known to those of skill in the art or that may be identified by those of skill in the art may be used in the assay. The cell surface protein may be endogenously expressed on the selected cell or it may be expressed from cloned DNA. Exemplary cell surface proteins include, but are not limited to, cell surface receptors and ion channels. Cell surface receptors include, but are not limited to, muscarinic receptors (e.g., human M2 (GenBank accession #M16404); rat M3 (GenBank accession #M16407); human M4 (GenBank accession W16405); human M5 (Bonner et al. (1988) Neuron 1:403-410); and the like); neuronal nicotinic acetylcholine receptors (e.g., the alpha 2, alpha 3 and beta 2 subtypes disclosed in U.S. Ser. No. 504,455 (filed Apr. 3, 1990), hereby expressly incorporated by reference herein in its entirety); the rat alpha 2 subunit (Wada et al. (1988) Science 240:330-334); the rat alpha 3 subunit (Boulter et al. (1986) Nature 319:368-374); the rat alpha 4 subunit (Goldman et al. (1987) cell 48:965973); the rat alpha 5 subunit (Boulter et al. (1990) J. Biol. Chem. 265:4472-4482); the rat beta 2 subunit (Deneris et al. (1988) Neuron 1:45-54); the rat beta 3 subunit (Deneris et al. (1989) J. Biol. Chem. 264: 6268-6272); the rat beta 4 subunit (Duvoisin et al. (1989) Neuron 3:487-496); combinations of the rat alpha subunits, beta subunits and alpha and beta subunits; GABA receptors (e.g., the bovine alpha 1 and beta 1 subunits (Schofield et al. (1987) Nature 328:221227); the bovine alpha 2 and alpha 3 subunits (Levitan et al. (1988) Nature 335:76-79); the gamma-subunit (Pritchett et al. (1989) Nature 338:582-585); the beta 2 and beta 3 subunits (Ymer et alo (1989) EMBO J. 8:1665-1670); the delta subunit (Shivers, B. D. (1989) Neuron 3:327-337); and the like); glutamate receptors (e.g., receptor isolated from rat brain (Hollmann et al. (1989) Nature 342:643-648); and the like); adrenergic receptors (e.g., human beta 1 (Frielle et al. (1987) Proc. Natl. Acad. Sci. 84.:7920-7924); human alpha 2 (Kobilka et al. (1987) Science 238:650-656); hamster beta 2 (Dixon et al. (1986) Nature 321:75-79); and the like); dopamine receptors (e.g., human D2 (Stormann et al. (1990) Molec. Pharm. 37:1-6); rat (Bunzow et al. (1988) Nature 336:783-787); and the like); NGF receptors (e.g., human NGF receptors (Johnson et al. (1986) Cell 47:545-554); and the like); serotonin receptors (e.g., human 5HT1a (Kobilka et al. (1987) Nature 329:75-79); rat 5HT2 (Julius et al. (1990) PNAS 87:928-932); rat 5HT1c (Julius et al. (1988) Science 241:558-564); and the like).

Reporter gene constructs are prepared by operatively linking a reporter gene with at least one transcriptional regulatory element. If only one transcriptional regulatory element is included, it must be a regulatable promoter. At least one of the selected transcriptional regulatory elements must be indirectly or directly regulated by the activity of the selected cell-surface receptor whereby activity of the receptor can be monitored via transcription of the reporter genes.

The construct may contain additional transcriptional regulatory elements, such as a FIRE sequence, or other sequence, that is not necessarily regulated by the cell surface protein, but is selected for its ability to reduce background level transcription or to amplify the transduced signal and to thereby increase the sensitivity and reliability of the assay.

Many reporter genes and transcriptional regulatory elements are known to those of skill in the art and others may be identified or synthesized by methods known to those of skill in the art.

A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnck (1979), Nature 282: 864-869) luciferase, and other enzyme detection systems, such as beta-galactosidase; firefly luciferase (deWet et al. (1987), Mot. Cell. Biol. 7:725-737); bacterial luciferase (Engebrecht and Silverman (1984), PNAS1: 4154-4158; Baldwin et al. (1984), Biochemistry 23:

3663-3667); alkaline phosphatase (Toh et al. (1989) Eur. J. Biochem. 182: 231-238, Hall et al. (1983) J. Mol. Appl. Gen. 2: 101).

Transcriptional control elements include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477-485), such as c-fos, Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires. new protein synthesis, and mRNAs transcribed from these genes have a short half-life. It is not necessary for all of these properties to be present.

V. Exemplary Uses of the Compounds of the Invention

In various embodiments, the present invention contemplates modes of treatment and prophylaxis which utilize one or more of the subject DAT inhibitors. These agents may be useful for decreasing or preventing the effects of defects in an animal which cause a movement disorder.

In various other embodiments, the present invention contemplates modes of treatment and prophylaxis which utilize one or more of the subject DAT inhibitors to alter defects which cause a movement disorder. The improvement and/or restoration of mental or physical state in an organism has positive behavioral, social, and psychological consequences.

In certain embodiments, the subject method can be used to treat patients who have been diagnosed as having or at risk of developing movement disorders.

Parkinson's disease is the second most common neurodegenerative disorder, affecting nearly 1 million people in North America. The disease is characterized by symptoms such as muscle rigidity, tremor and bradykinesia.

Early studies of Parkinson's disease showed unusual inclusions in the cytoplasm of neurons (i.e., Lewy bodies), occurring predominantly in the substantia nigra, which innervate the striatal region of the forebrain. Although Lewy bodies were also found in other neurodegenerative conditions, the presence of Lewy bodies in Parkinson's disease is accompanied by cell loss in the substantia nigra. This cell loss is considered to be the defining pathological feature of Parkinson's disease.

Epidemiological studies have reported geographic variation in Parkinson's disease incidence, leading to the search for environmental factors (Olanow and Talton, Ann. Rev. Neurosci., 22:123-144 [1998]). The recent discovery that 1-methyl-4-phenyl-1,2,3,6-tetrahydropyridine (MPTP) toxin causes a Parkinson's-like syndrome indistinguishable from the idiopathic disease suggests that Parkinson's disease may be caused by environmental factors (e.g., toxins and causative agents). (See e.g., Langston, Ann. Neurol., 44:S45-S52 [1998]).

Recent research has also identified genes associated with Parkinson's disease (Mizuno et al., Biomed. Pharmacother., 53(3):109-116 [1999]; Dunnett and Bjorklund, Nature 399 (6738 Suppl):A32-A39 [1999]); namely, the α-synuclein gene (Polymeropouos et al., Science 276:2045-2047 [1997]), the parkin gene (Kitada et al., Nature 392:605-608 [1998]), and the UCH-L1 thiol protease gene (Leroy et al., Nature 395:451-452 [1998]). Although additional chromosomal loci associated with the disease state have been identified, these chromosomal loci have not been analyzed at the molecular level. At present, the biochemical roles played by these gene products in both normal cells and in diseased neurons remain ambiguous, and no gene therapy protocols involving their use have been developed.

Furthermore, Parkinson's disease is associated with the progressive loss of dopamine neurons in the ventral mesencephalon of the substantia nigra (Shoulson, Science 282: 1072-1074 [1998]), which innervates the major motor-control center of the forebrain, the striatum. Although a gradual decline in the number of neurons and dopamine content of the basal ganglia is normally associated with increasing age, progressive dopamine loss is pronounced in people suffering from Parkinson's disease, resulting in the appearance of symptoms when about 70-80% of striatal dopamine and 50% of nigral dopamine neurons are lost (Dunnett and Bjorklund, supra). This loss of dopamine-producing neurons resulting in a dopamine deficiency is believed to be responsible for the motor symptoms of Parkinson's disease.

Although the cause of dopaminergic cell death remains unknown, it is believed that dopaminergic cell death is affected by a combination of necrotic and apoptotic cell death. Mechanisms and signals responsible for the progressive degeneration of nigral dopamine neurons in Parkinson's disease have been proposed (Olanow et al., Ann. Neurol., 44:S1-S196 [1998]), and include oxidative stress (from the generation of reactive oxygen species), mitochondrial dysfunction, excitotoxicity, calcium imbalance, inflammatory changes and apoptosis as contributory and interdependent factors in Parkinson's disease neuronal cell death.

Apoptosis (i.e., programmed cell death) plays a fundamental role in the development of the nervous system (Oppenheim, Ann. Rev. Neurosci., 14: 453-501 [1991]), and accelerated apoptosis is believed to underlie many neurodegenerative diseases, including Parkinson's disease (Baringa, Science 281: 1303-1304 [1998]; Mochizuki et al., J. Neurol. Sci., 137: 120-123 [1996]; and Oo et al., Neuroscience 69: 893-901 [1995]). In living systems, apoptotic death can be initiated by a variety of external stimuli, and the biochemical nature of the intracellular apoptosis effectors is at least partially understood.

Drugs used to treat Parkinson's disease include L-dopa, selegiline, apomorphine and anticholinergics. L-dopa (levo-dihydroxy-phenylalanine) (Sinemet) is a dopamine precursor which can cross the blood-brain barrier and be converted to dopamine in the brain. Unfortunately, L-dopa has a short half life in the body and it is typical after long use (i.e., after about 4-5 years) for the effect of L-dopa to become sporadic and unpredictable, resulting in fluctuations in motor function, dyskinesias and psychiatric side effects. Additionally, L-dopa can cause B vitamin deficiencies to arise.

Selegiline (Deprenyl, Eldepryl) has been used as an alternative to L-dopa, and acts by reducing the breakdown of dopamine in the brain. Unfortunately, selegiline becomes ineffective after about nine months of use. Apomorphine, a dopamine receptor agonist, has been used to treat Parkinson's disease, although is causes severe vomiting when used on its own, as well as skin reactions, infection, drowsiness and some psychiatric side effects.

Systemically administered anticholinergic drugs (such as benzhexyl and orphenedrine) have also been used to treat Parkinson's disease and act by reducing the amount of acetylcholine produced in the brain and thereby redress the dopamine/acetylcholine imbalance present in Parkinson's disease. Unfortunately, about 70% of patients taking systemically administered anticholinergics develop serious neuropsychiatric side effects, including hallucinations, as well as dyskinetic movements, and other effects resulting from wide anticholinergic distribution, including vision effects, difficulty swallowing, dry mouth, and urine retention. See e.g. Playfer, J. R., Parkinson's Disease, Postgrad Med J, 73; 257-264:1997 and Nadeau, S. E., Parkinson's Disease, J Am Ger Soc, 45; 233-240:1997.

Newer drug refinements and developments include direct-acting dopamine agonists, slow-release L-dopa formulations, inhibitors of the dopamine degrading enzymes catechol-O-methyltransferase (COMT) and monoamine oxidase B (MAO-B), and dopamine transport blockers. These treatments enhance central dopaminergic neurotransmission during the early stages of Parkinson's disease, ameliorate symptoms associated with Parkinson's disease, and temporarily improve the quality of life. However, despite improvements in the use of L-dopa for treating Parkinson's disease, the benefits accorded by these dopaminergic therapies are temporary, and their efficacy declines with disease progression. In addition, these treatments are accompanied by severe adverse motor and mental effects, most notably dyskinesias at peak dose and "on-off" fluctuations in drug effectiveness (Poewe and Granata, in Movement Disorders. Neurological Principles and Practice (Watts and Koller [eds]) McGraw-Hill, New York [1997]; and Marsden and Parkes, Lancet 1:345-349 [1977]). No drug treatments are currently available that lessen the progressive pace of nigrostriatal degeneration, postpone the onset of illness, or that substantively slow disability (Shoulson, supra).

Other methods for the treatment of Parkinson's disease involve neurosurgical intervention, such as thalamotomy, pallidotomy, and deep brain stimulation. The thalamic outputs of the basal ganglia are an effective lesion target for the control of tremor (i.e., thalamotomy). Thalamotomy destroys part of the thalamus, a brain region involved in movement control. Unilateral stereotactic thalamotomy has proven to be effective for controlling contralateral tremor and rigidity, but carries a risk of hemiparesis. Bilateral thalamotomy carries an increased risk of speech and swallowing disorders resulting.

Stereotactic pallidotomy, surgical ablation of part of the globus pallidus (a basal ganglia), has also be used with some success. Pallidotomy is performed by inserting a wire probe into the globus pallidus and heating the probe to destroy nearby tissue. Pallidotomy is most useful for the treatment of peak-dose diskinesias and for dystonia that occurs at the end of a dose.

Aside from surgical resection, deep brain stimulation, high frequency stimulating electrodes placed in the ventral intermedialis nucleus, has been found to suppress abnormal movements in some cases. A variety of techniques exist to permit precise location of a probe, including computed tomography and magnetic resonance imaging. Unfortunately, the akinesia, speech and gait disorder symptoms of Parkinson's disease, are little helped by these surgical procedures, all of which result in destructive brain lesions. Despite the development of modem imaging and surgical techniques to improve the effectiveness of these neurosurgical interventions for the treatment of Parkinson's disease tremor symptoms, the use of neurosurgical therapies is not widely applicable. For example, thalamotomy does not alleviate the akinetic symptoms which are the major functional disability for many people suffering from Parkinson's disease (Marsden et al., Adv. Neurol., 74:143-147 [1997]).

Therapeutic methods aimed at controlling suspected causative factors associated with Parkinson's disease (e.g., therapies which control oxidative stress and excitotoxicity) have also been developed. Clinical trials have shown that administration of antioxidative agents vitamin E and deprenyl provided little or no neuroprotective function (Shoulson et al., Ann. Neurol., 43:318-325 [1998]). Glutamate-receptor blockers and neuronal nitric oxide synthase (NOS) inhibitors have been proposed as therapies for Parkinson's disease, however, no experimental results from human studies have yet been published (Rodriguez, Ann. Neurol., 44:S175-S188 [1998]).

The use of neurotrophic factors to stimulate neuronal repair, survival, and growth in Parkinson's disease has also been studied, particularly the use of glial cell line-derived neurotrophic factor (GDNF). Although GDNF protein protects some dopamine neurons from death, it is difficult to supply GDNF protein to the brain. Furthermore, the use of such protein therapies in general is problematic, since protein molecules show rapid in vivo degradation, are unable to penetrate the blood-brain barrier, and must be directly injected into the ventricles of the patient's brain (Palfi et al., Soc. Neurosci. Abstr., 24:41 [1998]; Hagg, Exp. Neurol., 149:183-192 [1998]; and Dunnett and Bjorklund, supra). Other neurotrophic factors which may have therapeutic value have been proposed based on in vitro and animal model systems, including neurturin, basic fibroblast growth factor (bFGF), brain-derived neurotrophic factor (BDNF), neurotrophins 3 and 4/5, ciliary neurotrophic factor and transforming growth factor $\beta$ (TGF-$\beta$). However, the effectiveness of these therapies in humans remains unknown. At present, no single chemical compound or peptide has been reported to completely protect dopamine neurons from death by tropic factor withdrawal or neurotoxin exposure.

Cell replacement therapies have also received much attention as potential methods for treating Parkinson's disease (Freed et al., Arch. Neurol., 47:505-512 [1990]; Freed et al., N. Engl. J. Med., 327:1549-1555 [1992]; Lindvall et al., Science 247:574-577 [1990]; Spencer et al., N. Engl. J. Med., 327:1541-1548 [1992]; Widner et al., N. Engl. J. Med., 327: 1556-1563 [1992]; Lindvall, NeuroReport 8:iii-x [1997]; Olanow et al., Adv. Neurol., 74:249-269 [1997]; and Lindvall, Nature Biotechn., 17:635-636 [1999]). These neural grafting therapies use dopamine supplied from cells implanted into the striatum as a substitute for nigrostriatal dopaminergic neurons that have been lost due to neurodegeneration. Although animal models and preliminary human clinical studies have shown that cell replacement therapies may be useful in the treatment of Parkinson's disease, the failure of the transplanted neurons to survive in the striatum is a major impediment in the development of cell replacement therapies.

Various sources of dopaminergic neurons for use in the transplantation process have been tried in animal experiments, including the use of mesencephalic dopamine neurons obtained from human embryo cadavers, immature neuronal precursor cells (i.e., neuronal stem cells), dopamine secreting non-neuronal cells, terminally differentiated teratocarcinoma-derived neuronal cell lines (Dunnett and Bjorkland, supra), genetically modified cells (Raymon et al., Exp. Neurol., 144:82-91 [1997]; and Kang, Mov. Dis., 13:59-72 [1998]), cells from cloned embryos (Zawada et al., Nature Medicine 4:569-573 [1998]) and xenogenic cells (Bjorklund et al., Nature 298:652-654 [1982]; Huffaker et al., Exp. Brain Res., 77:329-336 [1989]; Galpem et al., Exp. Neurol., 140: 1-13 [1996]; Deacon et al., Nature Med., 3:350-353 [1997]; and Zawada et al., Nature Med., 4:569-573 [1998]). Nonetheless, in current grafting protocols, no more than 5-20% of the transplanted dopamine neurons survive.

Additional therapies are also available, such as physical therapy, occupational therapy, or speech/language therapy. Exercise, diet, nutrition, patient/caregiver education, and psychosocial interventions have also been shown to have a positive effect on the mental and/or physical state of a person suffering from Parkinson's disease.

Various methods of evaluating Parkinson's disease in a patient include Hoehn and Yahr Staging of Parkinson's Disease, Unified Parkinson Disease Rating Scale (UPDRS), and Schwab and England Activities of Daily Living Scale.

A person suffering from Parkinson's disease should avoid contraindicated and potentially contraindicated drugs such as antipsychotic drugs, Haloperidol (Haldol), Perphenazine (Trilafon), Chlorpromazine (Thorazine), Trifluoperazine (Stelazine), Flufenazine (Prolixin, Permitil) Thiothixene (Navane), Thioridazine (Mellaril); antidepressant drug, combination of Perphenazine and Amitriptyline (Triavil); antivomiting drugs, Prochlorperazine (Compazine), Metoclopramide (Reglan, Maxeran), Thiethylperazine (Torecan), Reserpine (Serpasil), Tetrabenazine (Nitoman); blood pressure drug, Alpha-methyldopa (Aldomet); anti-seizure drug, Phenyloin (Dilantin); mood stabilizing drug, lithium; and anti-anxiety drug, Buspirone (Buspar).

EXEMPLIFICATION

The invention now being generally described, it will be more readily understood by reference to the following examples which are included merely for purposes of illustration of certain aspects and embodiments of the present invention, and are not intended to limit the invention.

Example 1

Antagonism of Dopamine Receptors or Transporters & Functional Activity

Functional activity of the compounds was determined in vitro in cellular assays using recombinant human cell lines. Measurements of functional activity for serotonine uptake inhibition was determined in human HEK-293 cell lines according to the procedures of Gu et al. (*J. Biol. Chem.* 269: 27124, 1994) using fluoxetine ($EC_{50}$=57 nM) as the reference compound. Determination of functional activity for norephinephrine uptake inhibition was accomplished using an MDCK cell line according to the methods of Galli et al. (*J. Exp. Biol.* 198: 2197, 1995) with desipramine ($EC_{50}$=7 nM) as a reference compound. For determination of dopamine functional activity, a hDAT cell line was used as described by Giros et al. (*Mol. Pharmacol.* 42: 383, 1992) with nomifensine ($EC_{50}$=11 nM) as a reference compound.

TABLE I

In Vitro Selectivity - Functional Uptake Profiles

| | | CNS-28,100 | CNS-27,100 | CNS-28,001 | R-DDMS | R-DMS |
|---|---|---|---|---|---|---|
| HUMAN | DAT (nM) $EC_{50}$ | 1 | 1 | 5 | 100 | 30 |
| | NET (nM) $EC_{50}$ | 200 | 1000 | 5000 | 200 | 300 |
| | 5-HT (nM) $EC_{50}$ | 825 | 5000 | 5000 | 1500 | 1500 |
| RAT | DAT (nM) $EC_{50}$ | 50 | 80 | 300 | 100 | 70 |
| | NET (nM) $EC_{50}$ | 300 | 1000 | 5000 | 180 | 180 |
| | 5-HT (nM) $EC_{50}$ | 5000 | 5000 | 5000 | 1500 | 1500 |

Table I above listed the representative results obtained from several subject compounds, demonstrating superb in vitro selectivity for inhibiting functional uptake of DAT, as compared to uptake of related ligands (NET and 5-HT). For comparison, the results for two control compounds, R-DDMS and R-DMS, are also listed.

It is evident, based on these results, that the subject compounds are quite selective inhibitors of DAT uptake. For example, CNS-28,100 is a 200-fold and 825-fold more selective inhibitor for DAT than for NET and 5-HT, respectively. The selectivity for CNS-27,100 is 1000-fold (NET) and 5000-fold (5-HT), respectively. The selectivity for CNS-28, 001 is 1000-fold (NET) and 1000-fold (5-HT), respectively. In contrast, R-DDMS is only 2-fold more selective for DAT over NET, and 15-fold more selective for DAT over 5-HT. Similarly, R-DMS is 10-fold more selective for DAT over NET, and 50-fold more selective for DAT over 5-HT.

The ability of the compounds of the invention to displace norephinephrine ligands in vitro was determined by the methods of Galli et al (*J. Exp. Biol.* 198: 2197, 1995) using desipramine ($IC_{50}$=920 nM) as a reference compound. The displacement of dopamine, and serotonine ligands in vitro was determined by the methods of Gu et al. (*J. Biol. Chem.* 269: 7124, 1994) using GBR-12909 ($IC_{50}$(DA uptake)=490 nM, $IC_{50}$(5-HT uptake)=110 nM) as a reference compound. Other similar methods are also available in the art.

For example, in a typical uptake assay for measuring $IC_{50}$ of DAT, the assay is performed at room temperature in Krebs-Ringer's-HEPES (KRH) buffer (125 mM NaCl, 4.8 mM KCl, 1.2 mM $MgSO_4$, 1.2 mM $KH_2PO_4$, 1.3 mM $CaCl_2$, and 25 mM HEPES, pH 7.4), supplemented with 0.1% D-glucose, 1 mM ascorbic acid, 1 mM tropolone [catechol-O-methyltransferase (EC 2.1.1:6)-inhibitor] and 10 µM pargyline (monoamine oxidase-B inhibitor). Before the assay, cells expressing DAT are washed once with KRH and equilibrated for 5 min. The cells may be assayed in 24-well plates and incubated for 2-5 min. with tritiated amines. Nontransported inhibitors were preincubated for 5 min, and substrates were applied together with the tritiated substrate. The uptake assay is terminated with two washes of ice-cold KRH, and the accumulated radioactivity is recovered by lysing the cells in 0.2% SDS and 0.1 N NaOH and counting on a Liquid Scintillation Analyzer 1900 TR (Packard, Meriden, Conn.). Nonspecific uptake can be determined in the presence of 10 µM GBR12909 (for hDAT).

Experiments to determine the ionic requirements for DAT-mediated uptake are done in KRH buffer, substituting LiCl or choline Cl for NaCl (sodium-dependence) or substituting D-gluconates for NaCl and KCl, and $Ca(NO_3)_2$ for $CaCl_2$ (chloride dependence). Cells are washed twice with sodiumor chloride-free KRH before the assay (each wash step at least 5 min). In all transport assays, incubation periods and substrate concentrations are chosen such that uptake obeyed first-order rate kinetics.

$V_{max}$ values for amine uptake in stable transfected DAT-cells are determined in parallel assays for at least two amines per experiment and expressed as relative values.

Table II represents a typical result in table form. Specifically, the $IC_{50}$ for CNS-28,100 against DAT (SLC6A3) is 1 nM, while the $IC_{50}$ for the related NET (norepinephrine transporter or SLC6A2) and 5-HT receptors are 150 nM and 550 nM, respectively, indicating that the inhibitory effect of CNS-28,100 against DAT is not only highly effective, but also very specific (over 150-550 fold selectivity against related receptors).

Similar results were also obtained for CNS-27,100, where the $IC_{50}$ for DAT is also 1 nM, and the $IC_{50}$ for the related NET and 5-HT receptor are 175 nM and 1200 nM, respectively (175-1200 fold selectivity against related receptors).

Similar results were also obtained for CNS-28,001, where the $IC_{50}$ for DAT is 5 nM, and the $IC_{50}$ for the related NET and 5-HT receptor are 870 nM and 10,000 nM, respectively (174-2,000 fold selectivity against related receptors).

TABLE II

In Vitro Selectivity - Inhibition Profiles

| In vitro | CNS-28,100 | CNS-27,100 | CNS-28,001 |
|---|---|---|---|
| DAT (nM) $IC_{50}$ | 1 | 1 | 5 |
| NET (nM) $IC_{50}$ | 150 | 175 | 870 |
| 5-HT (nM) $IC_{50}$ | 550 | 1,200 | 10,000 |

In these experiments, CNS-27,100, CNS-28,001, and CNS-28,100 were all tested as racemic mixtures of enriched diastereomers.

The in vitro selectivity profile of two representative subject compounds, CNS-28,100 and CNS-27,100, are also tested against a panel of other receptors, including the $M_1$ receptor, Histamine $H_1$ receptor, sigma-1 ($\sigma_1$) receptor, $\beta_1$-adrenergic receptor, and dopamine $D_2$ receptor. Representative results are listed below in Table III:

TABLE III

In Vitro Selectivity Profiles for Other Receptors

| In vitro | CNS-28,100 | CNS-27,100 |
|---|---|---|
| $M_1$ (nM)$_h$ | 5000 | 5000 |
| Histamine $H_1$ (nM)$_h$ | 5000 | 5000 |
| Sigma $\sigma 1$ (nM)$_h$ | 5000 | 5000 |
| $\beta_1$-adrenergic (nM)$_h$ | 5000 | 5000 |
| $D_2$ (nM)$_h$ | 1000 | 1000 |

The results indicate that neither of these subject compounds are very selective for these other non-related or more distantly related receptors.

Example 2

In Vivo Efficacy of Several Illustrative Dopamine Transporter Inhibitors

In vivo efficacy of several illustrative DAT inhibitors of the instant invention, CNS-27,100, CNS-28,100, and CNS-28,200, were measured using standard forced swim test model using rat. The objective of this study was to assess the antidepressant effects of test compounds in the behaviral despair assay in rats using a modification of a method described by Porsolt R. D. et al. in *Behavioral despair in rats: a new model sensitive to antidepressant treatment*, Eur. J. Pharmacol., 47: 379-391, 1978; Porsolt et al., Nature 266: 730-732, 1977; and Porsolt et al., in Psychopharmacology, Olivier, Mos, and Slangen (eds) Birkhauser Verlag, Basel, pp. 137-159, 1991. Briefly, when mice (or rats) are forced to swim in a cylinder from which no escape is possible, they readily adopt a characteristic immobile posture and make no further attempts to escape except for small movements needed to keep floating. The immobility is considered by some to reflect a "depressive mood" (Porsolt et al., Nature 266: 730-732, 1977) in which animals cease to struggle to escape the aversive situation. The immobility induced by the procedure is influenced by a wide variety of antidepressants (Porsolt et al., in Psychopharmacology, Olivier, Mos, and Slangen (eds). Birkhauser. Verlag, Basel, pp. 137-159, 1991) and has a good predictive validity in that it detects antidepressants with different mechanisms of action (TCAs, SSRIs, MAOIs, and other atypical ones). The test is sensitive to muscle-relaxant (benzodiazepines) and sedative (neuroleptics) effects, leading to enhanced immobility (Porsolt et al., supra).

In a typical experiment, animals are placed singly into a cylinder (e.g. 46×30 cm) containing fresh water at about 20° C. for 6 minutes. The activity (or immobility) of the animal is measured by an observer minute by minute. In more detail, the animals were preconditioned in a pretest session, where the rats were individually forced to swim inside a vertical plexiglass cylinder containing water maintained at 19-20° C. After 15 minutes in the water, they were allowed to dry for 15 minutes in a heated enclosure. Twenty four hours later, the compounds were administered either intraperitoneally or orally to the animals. One hour after administration of the test compound, animals were put back into the cylinder containing water. The total duration of immobility was measured during the last 4 minutes of a 6 minute test.

The results are expressed as the percentage of variation of the total duration of immobility calculated from the mean value of the vehicle-treated group (% variation=[(immobility duration of vehicle−immobility duration of test compound)/(immobility duration of vehicle)]×100%). Only compounds which exibit a statistically significant variation (e.g. >30%) are considered effective in this in vivo model.

Figure 2:
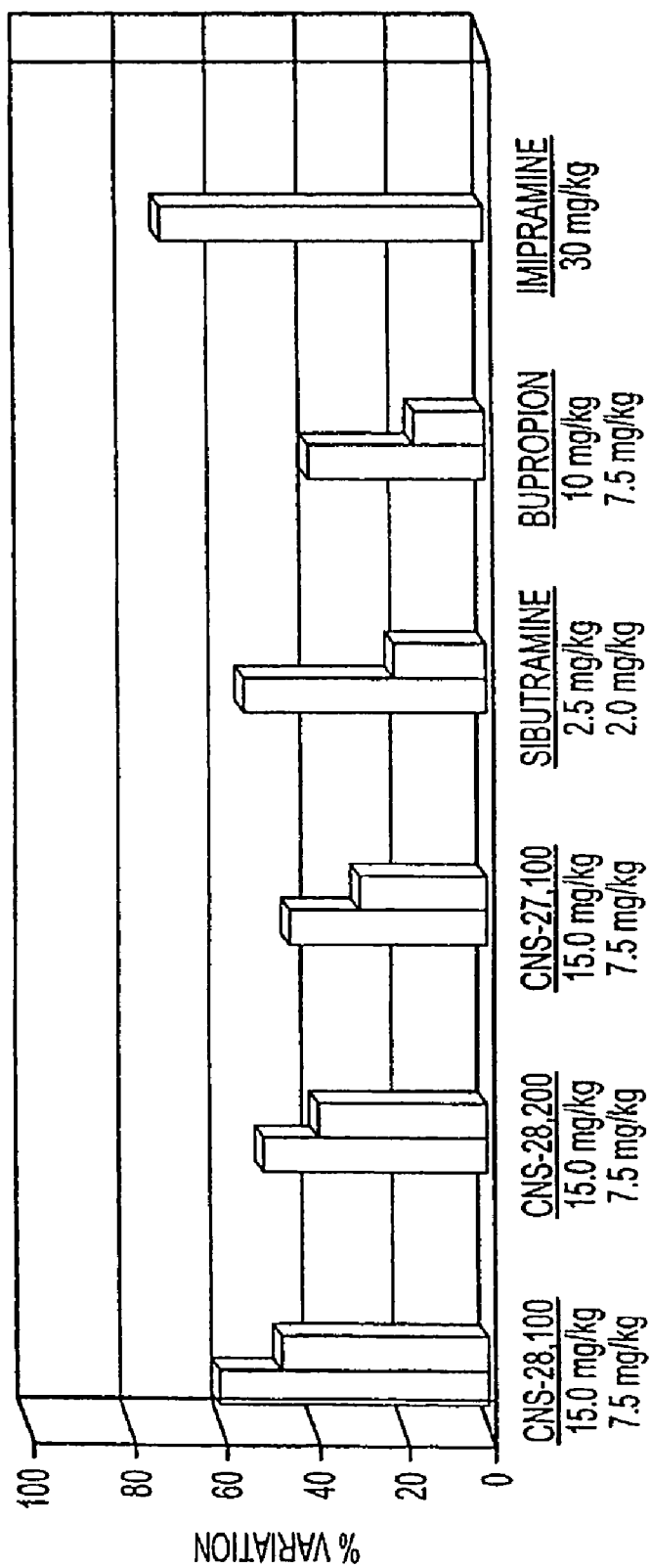
FIGS. 2-4 show in vivo efficacy of four illustrative dopamine transporter inhibitors, CNS-27,100, -28,002, -28,100, and -28,200, as measured by forced swim test using rats.

In order to measure the in vivo efficacy of inhibiting DAT in rats using the DAT inhibitor of the instant invention, one test inhibitor (CNS-27,100, CNS-28,100, or CNS-28,200) was injected i.p. as racemic mixtures of diastereomers into the animals, at various doses (e.g. 7.5 and 15 mg/kg). Sibutramine (2.0 and 2.5 mg/kg), Bupropion (7.5 and 10 mg/kg), and Imipramine (30 mg/kg) were similarly administered as controls. FIG. 2 indicates that at the doses tested, these DAT inhibitors performed equally well, if not better, than the commercial drugs Sibutramine, Bupropion, and Imipramine. Asterisks indicate highly statistical significant results.

Figure 4:
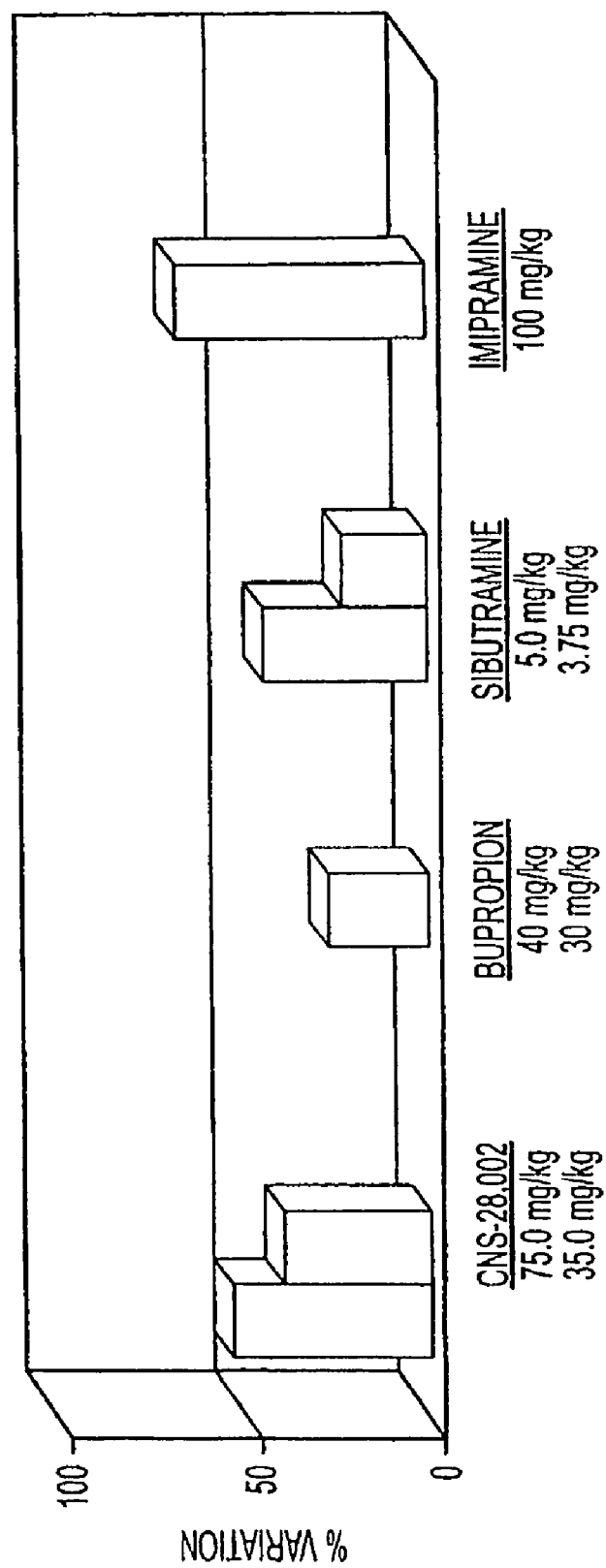

A fourth DAT inhibitor, CNS-28,002 was administered p.o. as a racemic mixture of diastereomers at either 35 or 75 mg/kg. Sibutramine (5.0 and 3.75 mg/kg), Bupropion (30 and 40 mg/kg), and Imipramine (100 mg/kg) were similarly administered as controls. FIG. 4 indicates that at the doses tested, CNS-28,002 performed equally well, if not better, than the commercial drugs Sibutramine, Bupropion, and Imipramine.

Figure 3:
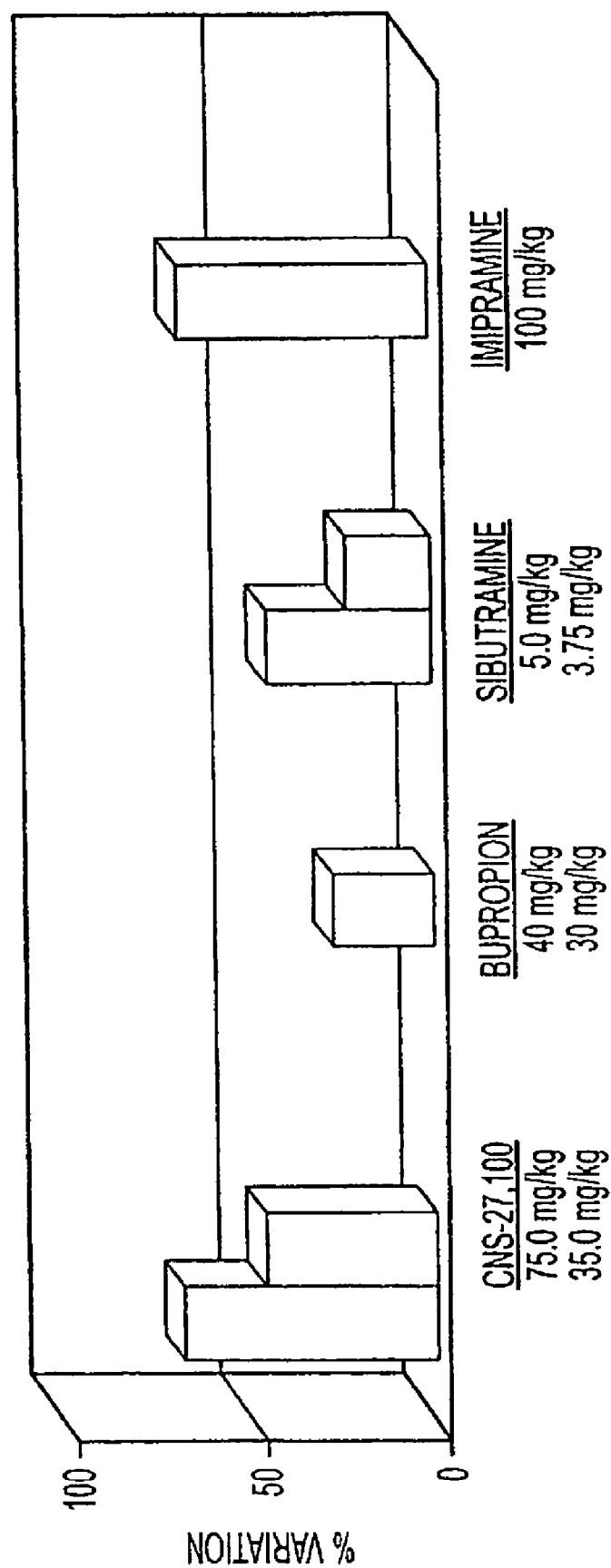

Similarly, CNS-27,100 was also administered p.o. as a racemic mixture of enriched (95:5) diastereomer at either 35 or 75 mg/kg. Sibutramine (5.0 and 3.75 mg/kg), Bupropion (30 and 40 mg/kg), and Imipramine (100 mg/kg) were similarly administered as controls. FIG. 3 indicates that at the doses tested, CNS-27,100 performed equally well, if not better, than the commercial drugs Sibutramine, Bupropion, and Imipramine.

Asterisks indicate highly statistical significant results.

Other in vitro profiles of the representative compounds CNS-28,100 and CNS-27,100 are listed below in Table IV.

TABLE IV

In Vivo Profiles for Representative Compounds

| In Vivo (Rat) | CNS-28,100 | CNS-27,100 |
|---|---|---|
| $T_{1/2}$ (i.v.) | 500 minutes | 200 minutes |
| Oral Bioavailability | 70% | 40% |
| Volume of Distribution | 10 L/kg | 6 L/kg |

Example 3

Toxicological Profiles of Illustrative Dopamine Transporter Inhibitors

An in vivo evaluation was carried out to determine the maximum tolerated dose of numerous test compounds in rat. The compounds were administered i.v., and the animals were then observed for 72 hours.

Table V summarizes the acute single-dose toxicological profile data for three DAT inhibitors of the instant invention, CNS-27,100, CNS-28,002, and CNS-28,200.

TABLE V

Acute Single-Dose Toxicological Profiles

| Acute Single Dose Toxicology | | CNS-27,100 | CNS-28,002 | CNS-28,200 |
|---|---|---|---|---|
| RAT (n = 5) | 30 mg/kg | No Significant Symptoms | No Significant Symptoms | No Significant Symptoms |
| | 90 mg/kg | No Significant Symptoms | No Significant Symptoms | No Significant Symptoms |
| | 120 mg/kg | No Significant Symptoms | No Significant Symptoms | Decrease grip strength and limb tone and convulsions |
| | 200 mg/kg | Decrease grip strength. Slight depression. | No Significant Symptoms | Convulsions |

Briefly, experimental rats, in groups of 5 animals, were administered with various doses of respective DAT inhibitors (e.g. 30, 90, 120, and 200 mg/kg), and the observed toxicological effects were recorded.

As is shown in Table V, rats tolerate doses below 120 mg/kg of CNS-27,100 well, with no significant observed symptoms associated with drug administration. At 200 mg/kg, animals showed decreased grip strength, and slight depression. Animals tolerates CNS-28,002 rather well, with no observed symptoms at the highest dose of 200 mg/kg. However, rats administered with CNS-28,200 showed decreased grip strength and limb tone and convulsions at 120 mg/kg, and convulsions at 200 mg/kg. But this dose is about 10 times the effective dose as shown in FIG. 2.

Multidose toxicology study was also conducted for CNS-27,100 (administered as enantiomerically enriched diastereomer), with Sibutramine as a control. Briefly, over the span of 7 days, 6 Sprague-Dawley rats (3 males and 3 females) were orally administered various doses of representative compound CNS-27,100, or the control compound Sibutramine at a dose volume of about 10 mL/kg body weight. The oral doses tested are 50 mg/kg/day, 100 mg/kg/day, 200 mg/kg/day, and 400 mg/kg/day. The representative results are listed below in Table VI.

TABLE VI

Multidose Toxicological Profiles

| 7-Day Multidose Oral Dosing Toxicology Study | | CNS-27,100 (enantiomerically enriched diastereomer) | Sibutramine |
|---|---|---|---|
| Sprague-Dawley Rats (n = 6; 3M/3F) Dose Volume: 10 mL/kg | 50 mg/kg/day | No significant symptoms. | Decreased grip strength. Slight depression |
| | 100 mg/kg/day | No significant symptoms. | Decreased grip strength. depression; 3 self mutilation |
| | 200 mg/kg/day | Decreased grip strength. Slight depression; 1 self mutilation | Decreased grip strength. Convulsions; 6 self mutilation 2 deaths |
| | 400 mg/kg/day | Decreased grip strength. Slight depression; 3 self mutilation | Convulsions; 4 deaths |

The results indicate that experimental animals tolerate CNS-27,100 better than Sibutramine at similar doses. For example, at 100 mg/kg/day, rats treated by CNS-27,100 did not display any significant symptoms. In contrast, rats treated by Sibutramine showed decreased grip strength, depression, and even 3 self-mutilation. Such symptoms were not seen in CNS-27,100-treated rats until the dose was raised 4-times higher to 400 mg/kg/day. At that dose, however, treatment with Sibutramine resulted in convulsions, and 4 deaths in 6 experimental animals.

EQUIVALENTS

Those skilled in the art will recognize, or be able to ascertain using no more than routine experimentation, many equivalents to the specific embodiments of the invention described herein. Such equivalents are intended to be encompassed by the following claims.

All patents, publications, and other references cited above are hereby incorporated by reference in their entirety.

The invention claimed is:

1. A compound represented by Formula I, or a pharmaceutically acceptable salt thereof:

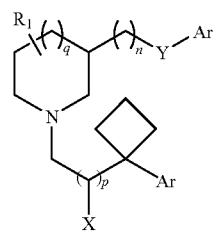

(I)

wherein, as valence and stability permit,

Ar, independently for each occurrence, represents a substituted aryl or heteroaryl ring and Ar is substituted with one or more groups selected from halogen, cyano, alkyl, alkenyl, alkynyl, aryl, hydroxyl, alkoxy, silyloxy, amino, nitro, thiol, imino, amido, phosphoryl, phosphonate, carboxyl, carboxamide, silyl, thioether, alkylsulfonyl, arylsulfonyl, sulfoxide, selenoether, ketone, aldehyde, ester, and —(CH$_2$)$_m$R$_2$, wherein m is an integer from 0 to 4 and R$_2$, independently for each occurrence, represents H or substituted or unsubstituted lower alkyl, cycloalkyl, heterocyclyl, aralkyl, heteroaralkyl, aryl, or heteroaryl;

X represents —H or —OR;

Y represents —O—;

R, independently for each occurrence, represents —H or lower alkyl;

R$_1$ represents one or more substituents positioned at the 4- and/or 6-position of the piperidine ring;

n is an integer from 0 to 2;

p is 0 or 1; and q is 1.

2. The compound of claim 1, wherein

R$_1$, independently for each occurrence, represents halogen, amino, acylamino, amidino, cyano, nitro, azido, ether, thioether, sulfoxido, -J-R$_2$, -J-OH, -J-lower alkyl, -J-lower alkenyl, -J-R$_2$, -J-SH, -J-NH$_2$, or substituted or unsubstituted lower alkyl, lower alkenyl, cycloalkyl, heterocyclyl, cycloalkylalkyl, heterocyclylalkyl, aryl, heteroaryl, aralkyl, or heteroaralkyl, or protected forms of the above;

R$_2$, independently for each occurrence, represents H or substituted or unsubstituted lower alkyl, cycloalkyl, heterocyclyl, aralkyl, heteroaralkyl, aryl, or heteroaryl; and J represents, independently for each occurrence, a chain having from 0-8 units selected from —C(R)$_2$—, —N(R)—, —O—, and —S—.

3. The compound of claim 1, wherein Ar is substituted with at least one halogen, cyano, alkyl, hydroxyl, alkoxy, alkenyl, alkynyl, aryl, nitro, thiol, imino, amido, carboxyl, thioether, alkylsulfonyl, arylsulfonyl, ketone, aldehyde, or ester group.

4. The compound of claim 1, wherein Ar is substituted with at least one halogen, cyano, alkyl, alkenyl, alkynyl, nitro, amido, carboxyl, alkylsulfonyl, ketone, aldehyde, or ester group.

5. The compound of claim 1, wherein Ar is substituted at the para position.

6. The compound of claim 1, wherein each occurrence of Ar is phenyl.

7. The compound of claim 1, wherein each occurrence of Ar is a phenyl substituted by one or more electron-withdrawing substituents.

8. The compound of claim 7, wherein the electron-withdrawing substituent is halogen, cyano, nitro, perfluoroalkyl or acyl group.

9. A compound, wherein the compound is

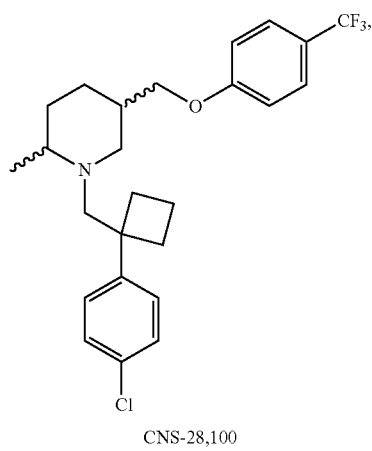

CNS-28,100

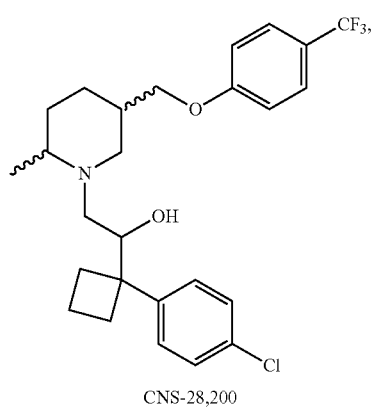

CNS-28,200

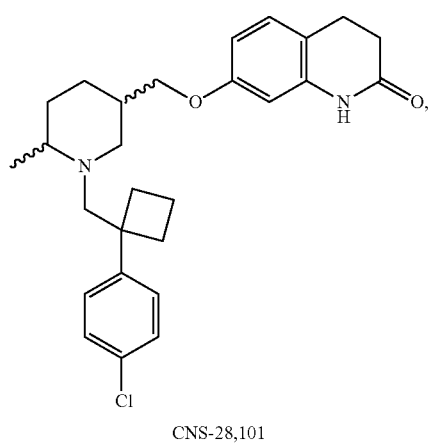

CNS-28,101

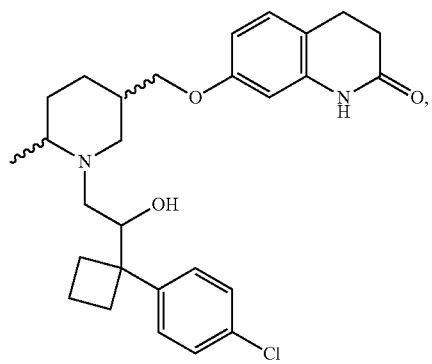

CNS-28,201

-continued

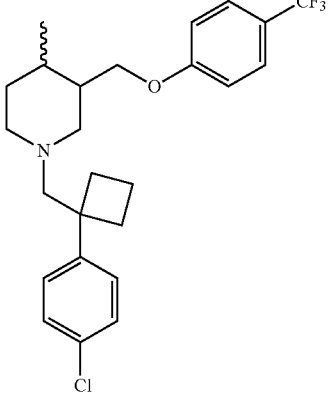
CNS-27,100

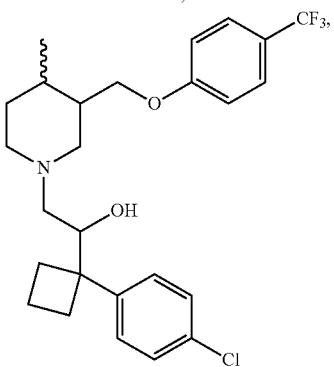
CNS-27,200

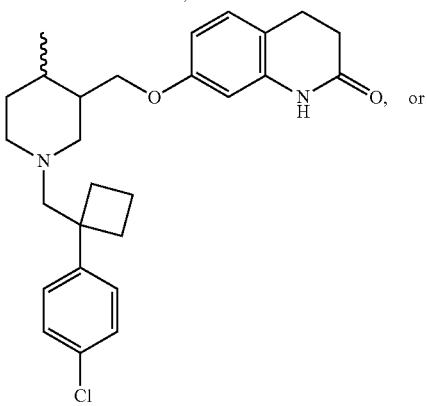
CNS-27,101

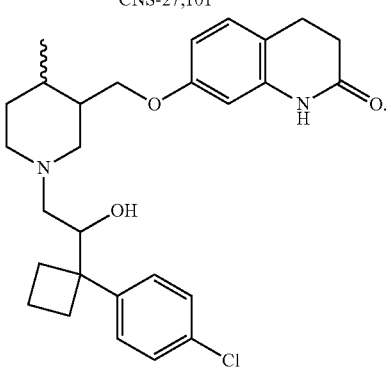
CNS-27,201

10. A compound represented by Formula I, or a pharmaceutically acceptable salt thereof:

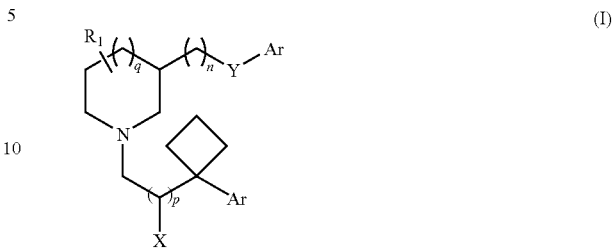

wherein, as valence and stability permit,

Ar, independently for each occurrence represents a substituted aryl or heteroaryl ring, and Ar is substituted with one or more groups selected from halogen, cyano, alkyl, alkenyl, alkynyl, aryl, hydroxyl, alkoxy, silyloxy, amino, nitro, thiol, imino, amido, phosphoryl, phosphonate, carboxyl, carboxamide, silyl, thioether, alkylsulfonyl, arylsulfonyl, sulfoxide, selenoether, ketone, aldehyde, ester, and —$(CH_2)_m R_2$, wherein m is an integer from 0 to 4 and $R_2$, independently for each occurrence, represents H or substituted or unsubstituted lower alkyl, cycloalkyl, heterocyclyl, aralkyl, heteroaralkyl, aryl, or heteroaryl;

X represents —H or —OR;

Y represents —O—;

R, independently for each occurrence, represents —H or lower alkyl;

$R_1$ represents one or more lower alkyl groups positioned at the 4- and/or 6-position of the piperidine ring;

n is an integer from 0 to 2;

p is 0 or 1; and q is 1.

11. The compound of claim 10, wherein Ar is substituted with at least one halogen, cyano, alkyl, hydroxyl, alkoxy, alkenyl, alkynyl, aryl, nitro, thiol, imino, amido, carboxyl, thioether, alkylsulfonyl, arylsulfonyl, ketone, aldehyde, or ester group.

12. The compound of claim 10, wherein Ar is substituted with at least one halogen, cyano, alkyl, alkenyl, alkynyl, nitro, amido, carboxyl, alkylsulfonyl, ketone, aldehyde, or ester group.

13. The compound of claim 10, wherein Ar is substituted at the para position.

14. The compound of claim 10, wherein each occurrence of Ar is phenyl.

15. The compound of claim 10, wherein each occurrence of Ar is a phenyl substituted by one or more electron-withdrawing substituents.

16. The compound of claim 15, wherein the electron-withdrawing substituent is halogen, cyano, nitro, perfluoroalkyl or acyl group.

* * * * *